United States Patent [19]

Mueller et al.

[11] Patent Number: 5,250,567
[45] Date of Patent: Oct. 5, 1993

[54] CYCLIC PHENOLIC THIOETHERS

[75] Inventors: Richard A. Mueller, Glencoe; Richard A. Partis, Evanston, both of Ill.

[73] Assignee: G. D. Searle & Co., Chicago, Ill.

[21] Appl. No.: 903,832

[22] Filed: Jun. 24, 1992

Related U.S. Application Data

[62] Division of Ser. No. 697,849, May 9, 1991, Pat. No. 5,147,893.

[51] Int. Cl.⁵ .................. A61K 31/34; C07D 307/20
[52] U.S. Cl. ...................... 514/473; 549/476; 549/417; 514/460
[58] Field of Search ............ 549/65, 66, 476, 417; 514/445, 473, 460

[56] References Cited

U.S. PATENT DOCUMENTS

| 3,574,512 | 4/1971 | Weber et al. | 549/66 |
|---|---|---|---|
| 4,029,812 | 6/1977 | Wagner et al. | 424/298 |
| 4,076,841 | 2/1978 | Wagner et al. | 424/324 |
| 4,078,084 | 3/1978 | Wagner et al. | 424/324 |
| 4,153,803 | 5/1979 | Thiele et al. | 560/57 |
| 4,621,098 | 11/1986 | Umminger et al. | 514/562 |
| 4,711,903 | 12/1987 | Mueller et al. | 514/381 |
| 4,755,524 | 7/1988 | Mueller et al. | 514/381 |
| 4,801,611 | 1/1989 | Chinn et al. | 514/532 |
| 5,064,860 | 11/1991 | Mueller et al. | 514/568 |
| 5,082,854 | 1/1992 | Mueller et al. | 514/537 |

FOREIGN PATENT DOCUMENTS

| 0131221 | 1/1985 | European Pat. Off. | 514/381 |
|---|---|---|---|
| 0218782 | 4/1987 | European Pat. Off. | 549/65 |
| 0293900 | 12/1988 | European Pat. Off. | 514/532 |
| 0339688 | 11/1989 | European Pat. Off. | 549/65 |
| 49-116035 | 11/1974 | Japan | 514/381 |
| 62-81343 | 4/1987 | Japan | 514/381 |
| 4-69375 | 3/1992 | Japan | 549/470 |

OTHER PUBLICATIONS

Chemical Abstracts, vol. 117, No. 1, Abstract No. 8303f, p. 8306, Jul. 6, 1992.
Caglioti et al., "Acid Decomposition of Tosylazocyclohex-1-ene and 3-Tosylazocholeste-3,5-diene," *J. Org. Chem.*, 38(5):920-923.

(List continued on next page.)

*Primary Examiner*—C. Warren Ivy
*Assistant Examiner*—Zinna N. Davis
*Attorney, Agent, or Firm*—Roberta L. Hastreiter; Roger A. Williams

[57] ABSTRACT

The compounds of the present invention comprise substituted phenolic thioethers represented by the formula (I):

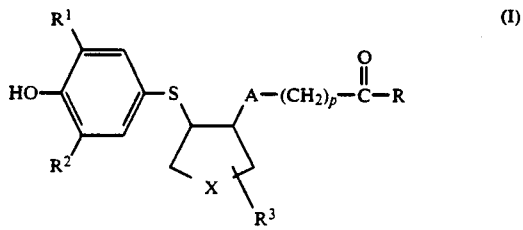

wherein: $R^1$ and $R^2$ are the same or different and independently represent tert-alkyl or phenyl; $R^3$ represents hydrogen or alkyl; X represents $-(CH_2)_w-B-(CH_2)_y-$ wherein B represents O, S, or $CH_2$ and w and y can each independently be an integer from 0 to 3 with the proviso that the sum of $w+y$ is equal to or less than 3; A represents O or $S(O)_n$ wherein n is 0, 1 or 2; p is an integer from 1 to 4; and R represents alkyl; OH; $OR^4$ wherein $R^4$ is alkyl of 1 to 4 carbon atoms; $NR^5R^6$ wherein $R^5$ is hydrogen or alkyl and $R^6$ is hydrogen, alkyl, heterocyclealkyl in which the heterocyclic ring may optionally be substituted; cycloalkyl; substituted cycloalkyl; phenyl; substituted phenyl; phenylalkyl; or substituted phenylalkyl; or $NR^5R^6$ together form a heterocyclic ring which may optionally be substituted; or R is $(CH_2)_tCOOR^7$ wherein t is an integer from 1 to 4 and $R^7$ is hydrogen or alkyl of 1 to 4 carbon atoms; and the pharmaceutically acceptable salts and stereoisomers or geometric isomers thereof. The compounds of the present invention are inhibitors of 5-lipoxygenase and therefore, are useful in the treatment of local and systemic inflammation, allergy and hypersensitivity reactions and other disorders in which agents formed in the 5-lipoxygenase metabolic pathway are involved.

19 Claims, No Drawings

OTHER PUBLICATIONS

Davis, F. A., et al. "Chemistry of the Sulfur-Nitrogen Bond. VII. Rearrangement of Sulfenimines (S-Aryl Thiooximes) to Beta-Keto Sulfides. Attempted Synthesis of Benzo[b]thiophenes," *J. Org. Chem.*, 39(6):807-809 (1974).

Kal'Yan, et al., *Izv. Akad Mauk SSSR Ser Kim*, 2:378-86 (1982).

MacKenzie, N. E., et al. "Ring Contractions of Thiochroman-4-ones and Thiochromen-4-ones," *J. Chem. Soc. Perkin Trans.* 1(2):395-402.

Magerramov, et al., "Reactions to Arenesulfenyl Chloride with Methylenecycloalkanes and Vinylcyclopropane," *Zh. Organ. Khim*, 26(11):2333-41 (1990).

Mukaiyama, T., et al., "Reactions of Mercuric salts with Bis(diethylthiocarbamoyl) Disulfide and Benzenesulfenyl Chloride," *J. Org. Chem.* 33(6): 2242-5 (1968).

Pushin, et al., "Doping Effect and Acid Catalysis in the Addition of Sulfenyl Chlorides to Cyclohexene in Acetic Acid," *Zh. Organ. Khim.*, 27:(7):1473-8 (1991).

Zefirov, et al., "A New Method of Increasing the Effective Electrophilicity of Weak Electrophiles", p. 223, *Zhurnal Organicheskai, Khimi*, vol. 13, No. 2, pp. 245-250 (Feb. 1977).

Zefirov, N. S., et al., "Stereochemical Studies-XX Conformations of 1,2-Trans-Disubstituted Cyclohexanes," *Tetrahedron*, 32:1211-1219 (1976).

Medvedev, A., et al., *Khimiya i Khimicheskaya Tekhnologiya*, 20, pp. 568-675 (1977).

Kocan, G., et al., Inflammation Research Association, Fifth International Conference Poster Session, Abstract 20, Sep. 23-27, 1990.

Kukreja, R., et al., *Circulation Research*, 59(6):612-619 (1986).

Katayama, K., et al., *Agents and Actions*, 21(3/4):269-271 (1987).

Beiemond, P., et al., *Scand J. Rheumatology*, 19:151-156 (1990).

Kreutner, W., et al., *J. Pharmacol. Exp. Ther.*, 247(3):997-1003 (1988).

Cross, C. E., et al., *Ann. Int. Med.*, 107:526-545 (1987).

Ward, P. A., et al., *Free Radical Biology & Medicine*, 5:403-408 (1988).

Cencetti, M., et al., *Clinical Rheumatology*, 9(1):51-55 (1990).

Auer, D. E., et al., *J. Vet. Pharmacol. Therap.*, 13(1):59-66 (1990).

Kanofsky, J. R., *Chem. Biol. Interactions*, 70:1-28 (1989).

Shepherd, V. L., *Semin. Respir. Infect.* (United States) Jun. 1986, 1(2), pp. 99-106.

Kanai, Kenichi, CA 107:197783q.

Katsumi, Ikuo, "Studies on Stryene Derivatives," *Chem. Pharm. Bull.*, 34 (4):619-1627 (1986).

CYCLIC PHENOLIC THIOETHERS

This is a continuation division of application Ser. No. 07/697,849, filed May, 9, 1991, now U.S. Pat. No. 5,147,893.

BACKGROUND OF THE INVENTION

1. Field of the Invention

The present invention relates to cyclic phenolic thioethers and more particularly relates to the novel compounds of Formula I which are 5-lipoxygenase inhibitors. The compounds of Formula I are useful, for example, as anti-inflammatory and anti-allergy agents and in the treatment of hypersensitivity reactions, psoriasis, asthma, and related disorders and conditions in which physiologically active agents formed in the 5-lipoxygenase metabolic pathway are involved. Compounds of the present invention may be useful in treating arthritis, asthma, and psoriasis. Some compounds of the present invention also stimulate superoxide generation and may be useful as adjunctive therapeutic agents in the treatment of infections. Other compounds of the present invention inhibit superoxide generation and may be useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

2. Background Information

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

Aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, antipyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity; skin rashes; syndrome of abdominal pain, fever, chills, nausea and vomiting; and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been an effort to develop new drugs which selectively block the formation of the mediators of these conditions, and the present invention provides new chemical entities which are inhibitors of the 5-lipoxygenase pathway and are useful in the treatment of asthma, rheumatoid arthritis, psoriasis, and other allergic, hypersensitivity, and inflammatory conditions.

The present invention provides compounds which block the 5-lipoxygenase metabolic pathway and, therefore, block the formation of the leukotrienes responsible for allergy and inflammation, and represent therapeutic agents which are useful in the treatment of allergic and hypersensitivity reactions and inflammation, alone, or also may be utilized in combination with other lipoxygenase inhibitors or with cyclooxygenase inhibitors such as the non-steroidal anti-inflammatory agents.

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications,* and *Free Radical Biology and Medicine.*

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," ANN. INT. MED., 107:526-545 (1987) (see Table 1, p. 527) and Ward, P. A., et al., "Oxygen Radicals, Inflammation, and Tissue Injury," FREE RADICAL BIOLOGY & MEDICINE, 5:403-408 (1988). Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, radiation injury and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells such as neutrophils, monocytes and macrophages, eosinophils, and endothelial cells; and antioxidation reactions; and exogenous, such as redox-cycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Those compounds of the present invention which inhibit superoxide generation may be useful in the treatment of diseases mediated by superoxide generation.

There are also some conditions in which the generation of superoxide may be desirable. Those compounds of the present invention which stimulate superoxide generation may be useful in the adjunctive therapy of microbial infections. See Goodman and Gilman's, The Pharmacological Basis of Therapeutics (7th Edition, 1985) p. 660-673; P. A. Ward, et. al., "Oxygen Radicals, Inflammation and Tissue Injury," FREE RADICAL BIOLOGY & MEDICINE, 5: 403-408 (1988); and C. E. Cross, et. al., "Oxygen Radicals and Human Disease,"; ANN. INT. MED., 107: 526-545 (1987). Generation of reactive oxygen species is a critical event in successful host defense against invading organisms. Both neutrophils and macrophages rely on a variety of oxidants to damage bacterial constituents (see V. L. Shepherd, "The role of the respiratory burst of phagocytes in host defense," SEMIN. RESPIR. INFECT. (United States) Jun. 1986, 1(2) p. 99-106.

Various thioether compounds have been described previously. For example, U.S. Pat. No. 4,711,903 and its continuation-in-part, U.S. Pat. No. 4,755,524 disclose compounds of the formula

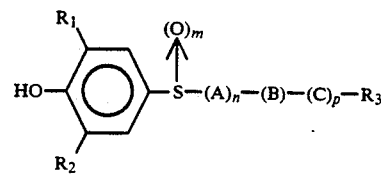

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase and are useful in the treatment of local and systematic inflammation, allergy and hypersensitivity reactions and other disorders in which agents formed in the 5-lipoxygenase metabolic pathway are involved.

U.S. Pat. No. 4,621,098 and its equivalent, European Patent Application Publication No. 0131221 disclose compounds of the formula

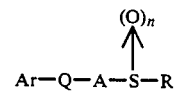

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene, and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0 without mention of any preference among the numerous possible substituents for R or substituted phenyl as Ar. In contrast to the invention disclosed in the foregoing publication, the compounds of the present invention all have cycloalkyl at the position corresponding to A as well as having di(tertiary)-alkyl or diphenyl groups as substituents on the phenol moiety corresponding to the substituted Ar group in the above publication which, as described therein, may or may not comprise a phenol.

U.S. Pat Nos. 4,029,812, 4,076,841 and 4,078,084 disclose compounds of the formula

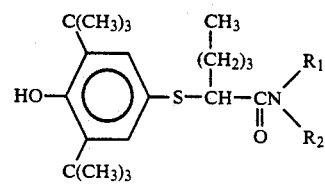

comprising 2-(3,5-di-tert -butyl-4-hydroxy-phenyl) thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythiophenol, and hydrogen sulfide to acrylate derivatives have been described. See Medvedev et al., Khimiya; Khimicheskaya Tekhnologiya, Volume 20, (1977), pp. 568-574.° The compounds resulting from the foregoing process have the general formulas $RS(CH_2)_nX$ and $S(CH_2CH_2X)_2$ in which R is 3,5-di-tert-butyl-4-hydroxyphenyl and X represents, for example, $-C\equiv N$, $NH_2$, $CH(OH)CH_2Cl$, OH, COCl and various carboxy, carboxylate and amide functions. Compounds of formula I according to the present invention or 5-lipoxygenase activity for structurally related compounds are not disclosed.

U.S. Pat No. 4,153,803 discloses cholesterol-lowering phenoxyalkanoic acid esters of the formula

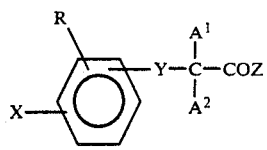

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

SUMMARY OF THE INVENTION

It is, therefore, a primary object of the present invention to provide novel cyclic phenolic thioethers pharmaceutical compositions containing them and methods of using them, as well as intermediates for producing them.

It is a further object of the present invention to provide methods for treating lipoxygenase mediated conditions and for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide dosage unit forms adapted for, e.g., oral, topical, and/or parenteral administration and useful in the treatment, management and mitigation of allergies, inflammation, psoriasis and hypersensitivity reactions and related disorders and lipoxygenase mediated conditions in which physiologically active agents formed in the arachidonic acid metabolic pathway are involved.

Those compounds of the present invention which inhibit superoxide generation may be useful in the therapeutic or prophylactic treatment of disease conditions which are mediated wholly or partly by superoxide generation such as adult respiratory distress syndrome, superoxide mediated inflammatory or allergic conditions, and other medical conditions which are caused by or aggravated by superoxide.

Those compounds of Formula I which are stimulators of superoxide generation in neutrophils may be useful in the therapeutic or prophylactic treatment of disease conditions in which superoxide generation is an important factor.

Although it has been speculated that 5-lipoxygenase may be involved in superoxide generation, the ability of some compounds, which inhibit 5-lipoxygenase, to stimulate superoxide generation in neutrophils while others inhibit superoxide generation indicates that superoxide generation is not governed by 5-lipoxygenase. Thus the activity of the compounds of Formula I in stimulating or inhibiting superoxide generation is not related to the ability to inhibit 5-lipoxygenase. In general those compounds of Formula I which are carboxylic acids inhibit superoxide generation and those compounds which are heterocycle alkyl amides inhibit superoxide generation. Compounds of Formula I which are readily hydrolyzable to the carboxylic acid upon oral administration may also act as prodrugs which would be converted to superoxide inhibitors by stomach acid.

The present invention provides a method by which neutrophil activation and the generation of superoxide anions are accomplished utilizing compounds of Formula I having the ability to stimulate superoxide generation. Accordingly these compounds of Formula I are useful in the design and testing of anti-inflammatory properties of other pharmacologically active agents.

The ability to produce superoxide which may itself be microbicidal or which is then converted to toxic oxidants such as $H_2O_2$,.OH, and singlet oxygen is important to the phagocytic killing mechanisms which enable neutrophils and macrophages to kill bacteria and parasites through phagocytosis.

Therefore, compounds of Formula I which stimulate superoxide generation may be useful in the adjunctive therapy of microbial infections. The compounds may also be useful in treating conditions such as Chediak-Higashi Syndrome in which the patient's macrophages and polymorphs are only weakly active causing the patients to suffer from recurring infections involving organisms with normally low pathogenicity. Compounds of Formula I may also be useful in the adjunctive therapy of patients whose immune systems have been weakened or impaired by disease or by chemotherapy or radiation therapy and who are more subject to microbial infections.

DETAILED DESCRIPTION OF THE PREFERRED EMBODIMENTS

These and other similar objects, advantages and features are accomplished according to the products, compositions and methods of the invention comprising compounds of the formula

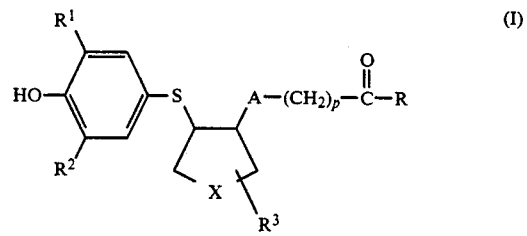

and the pharmaceutically acceptable slats thereof wherein $R^1$ and $R^2$ are the same or different and independently represent tert-alkyl or phenyl; $R^3$ represents hydrogen or alkyl; X represents $-(CH_2)_w-B-(CH_2)_y-$ wherein B represents O, S, or $CH_2$ and w and y can each independently be an integer from 0 to 3 with the proviso that the sum of w+y is equal to or less than 3; A represents O or S(O)$_n$ wherein n is 0, 1, or 2; p is an integer from 0 to 4; and R represents:
  (a) alkyl;
  (b) OH;
  (c) OR$^4$ wherein R$^4$ is alkyl of about 1 to about 4 carbon atoms;
  (d) NR$^5$R$^6$ wherein R$^5$ is hydrogen or alkyl, and R$^6$ is hydrogen, alkyl, heterocyclealkyl, substituted heterocyclealkyl, cycloalkyl, substituted cycloalkyl, phenyl, substituted phenyl, phenylalkyl, or substituted phenylalkyl, or NR$^5$R$^6$ together form a heterocyclic ring which may optionally be substituted; or
  (e) (CH$_2$)$_t$COOR$^7$ wherein t is an integer from 1 to 4 and R$^7$ is hydrogen or alkyl of 1 to 4 carbon atoms.

Included in the present invention are compounds of the formula

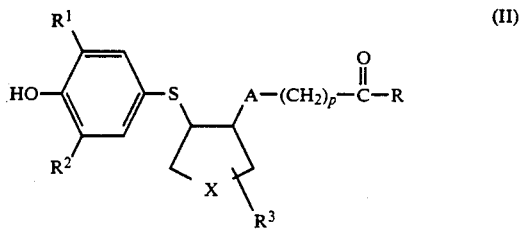

and the pharmaceutically acceptable salts thereof wherein R$^1$ and R$^2$ are the same or different and independently represent tert-alkyl or phenyl; R$^3$ represents hydrogen or alkyl of 1 to 4 carbon atoms; X represents O, S, or (CH$_2$)$_m$ wherein m is 1 or 2; A represents O or S(O)$_n$ wherein n is 0, 1, or 2; p is an integer from 0 to 4; and R represents:
  (a) alkyl of 1 to 4 carbon atoms;
  (b) OH;
  (c) OR$^4$ wherein R$^4$ is alkyl of 1 to 4 carbon atoms;
  (d) NR$^5$R$^6$ wherein R$^5$ is hydrogen or alkyl and R$^6$ is hydrogen, alkyl or heterocycle alkyl, or NR$^5$R$^6$ together form a heterocyclic ring which may optionally be substituted; or
  (e) (CH$_2$)$_t$ COOR$^7$ wherein t is an integer from 1 to 4 and R$^7$ is hydrogen or alkyl of 1 to 4 carbon atoms.

Also included in the present invention are novel intermediates of the Formula III

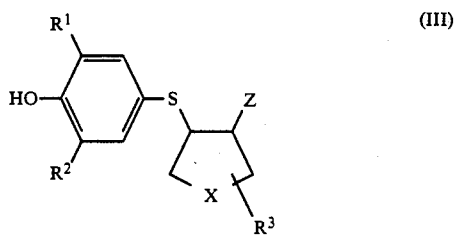

wherein R$^1$, R$^2$, R$^3$ and X, are defined as Formula I, and Z represents hydroxy, halogen, sulfate ester, or perfluoroacyl ester.

The compounds of Formula III are useful as intermediates for making compounds of Formula I and in addition are biologically active 5-lipoxygenase and/or cyclooxygenase inhibitors.

More preferred compounds of the present invention are compounds of the formula IV:

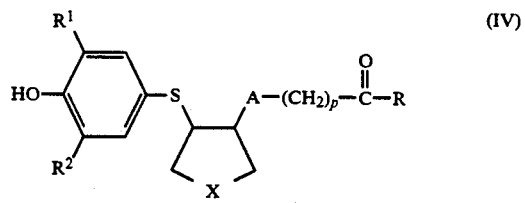

wherein R$^1$ and R$^2$ are the same or different and independently represent tert-alkyl or phenyl; X is O or (CH$_2$)$_m$ wherein m is 1 or 2, A is S or O; p is an integer from 0 to 2; and R is:
  (a) alkyl of 1 to 4 carbon atoms;
  (b) OH;
  (c) OR$^4$ wherein R$^4$ is alkyl of 1 to 4 carbon atoms; or
  (d) NR$^5$R$^6$ wherein R$^5$ is hydrogen or alkyl of 1 to 6 carbon atoms and R$^6$ is hydrogen, alkyl of 1 to 6 carbon atoms or heterocyclealkyl wherein the alkyl moiety has 1 to 4 carbon atoms, or NR$^5$R$^6$ together form a heterocyclic ring which may optionally be substituted; and the pharmaceutically acceptable salts thereof.

Particularly preferred compounds of formula I are those wherein R$^1$ and R$^2$ are both tert-alkyl; X is O or (CH$_2$)$_m$ wherein m is 1 or 2; A is sulfur; p is 1 or 2; and R is:
  (a) OH;
  (b) OR$^4$ wherein R$^4$ is alkyl of 1 to 4 carbon atoms; or
  (c) NR$^5$R$^6$ wherein R$^5$ is hydrogen or alkyl of 1 to 6 carbon atoms and R$^6$ is hydrogen, alkyl of 1 to 6 carbon atoms or heterocyclealkyl wherein the alkyl moiety has 1 to 4 carbon atoms;
and the pharmaceutically acceptable salts thereof.

Compounds of Formula I can possess one or more asymmetric atoms and are thus capable of existing in the form of optical isomers as well as in the form of racemic or nonracemic mixtures thereof. The optical isomers can be obtained by resolution of the racemic mixtures by conventional processes. Included in the family of compounds of Formula I and Formula III are isomeric forms including diastereoisomers, geometric isomers, and the pharmaceutically acceptable salts thereof.

The term "tert-alkyl" as used herein in reference to R$^1$ and R$^2$ refers to branched chain alkyl moieties of from about 4 to about 10 carbon atoms having a tertiary carbon atom attached to the phenyl ring substituted by R$^1$ and R$^2$. Examples of such groups are tert-butyl, i.e., 1,1-dimethylethyl, 1-1-dimethylpropyl, 1-methyl-1-(ethyl)pentyl, 1,1-diethylpropyl, 1-ethyl-1-(propyl)butyl and the like.

The term "alkyl" defines straight or branched chain monovalent hydrocarbon radicals having between about 1 to 6 carbon atoms including, for example, methyl, ethyl, propyl, isopropyl, butyl, t-butyl, pentyl, 1-methylbutyl, isopentyl, neopentyl, hexyl, etc.

The terms "heterocycle" and "heterocyclic ring" as used herein refer to aromatic or nonaromatic heterocyclic rings which contain one or more heteroatoms and include but are not limited to pyridine, piperazine, piperidine, morpholine, azabicycloalkyl, e.g., 3-azabicyclo[3,2,2]nonane, azatricycloalkyl, 1,2,3,4-tetrahydroisoquinoline, 5,6,11,12-tetrahydrodibenz[b,f]azocine, iminostilbene, and the like which may optionally be substituted with one or more substituents selected from alkyl, phenyl, substituted phenyl, phenylalkyl, heterocycle, cycloalkyl, halogen, hydroxy and lower alkoxy.

The terms "substituted phenyl" and "substituted phenylalkyl" as used herein refer to phenyl or phenylalkyl moieties in which the phenyl ring is substituted by one or more substituents selected from alkyl, hydroxy, alkoxy, halogen, alkylamino, dialkylamino, phenyl and alkyl carbonyl.

The term "cycloalkyl" refers to cycloalkyl rings of 3 to 10 carbon atoms and includes but is not limited to cyclopentyl, cyclohexyl, adamantane, norbornane and the like which may optionally be substituted by 1 or more substituents selected from alkyl, hydroxy, alkoxy, and halogen.

The term "halogen" refers to chlorine, bromine, fluorine, and iodine.

The expression "pharmaceutically acceptable salts" is intended to include those salts capable of being formed with the compounds of the present invention, e.g., when R represents OH, $NR^5R^6$ or alkyl carboxyl, without materially altering the chemical structure or pharmacological properties thereof. Such salts include inorganic and organic cations or acid addition salts, such as sodium, potassium, calcium, ammonium, alkylammonium, quaternary ammonium, triethanolamine, lysine, hydrochloric, hydrobromide, etc. well known to those skilled in the art. The foregoing salts are prepared in the conventional manner by neutralization of the compounds of formula I with the desired base or acid.

The compounds of the present invention can be administered to a patient in such oral dosage forms as tablets, capsules, pills, powders, granules, elixirs, or syrups as well as aerosols for inhalation. Likewise, administration may be effected intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered transdermally or topically to treat proliferative skin conditions such as psoriasis. The daily dosage may be administered in a single dose or in equal divided doses three or four times daily.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are prepared from readily available starting materials by any of the following alternate processes in a conventional manner. The following reaction schemes describe methods which can be employed for preparing the compounds of formula I, including starting materials, intermediates, and reaction conditions.

As shown in part (1) of Scheme A, a mercaptan (V) can be reacted with an oxabicyclo compound (VI) to give the intermediate (III) which may then be reacted with a monohaloacid in a base or alternatively with a thiol acid in an acid to obtain a product acid of type (VII). Epoxides of type (VI) are readily prepared by oxidation of a double bond with peroxides such as m-chloroperbenzoic acid, peracetic acid, per trifluoroacetic acids, hydrogen peroxide, t-butyl hydroperoxide and the like. Base induced cyclization of halohydrins, obtained by treatment of double bonds with mineral acids, also produces epoxides. In addition, epoxides can be used as starting materials for the preparation of halohydrins which can also be used to produce compounds of type III, following reaction with, for example, a mercaptan. Most bases can be used for the preparation of III, for example, hydroxides, tert-amines, heterocyclic amines, dimethylaminopyridines, hydrides, lithium alkyls, lithium amides and the like, since the thiolate anion is an exceptional nucleophile. Non-nucleophilic bases are preferred for the conversion of III into VII in the presence of an electrophilic reagent such as a substituted halo alkyl group.

Compound III may also be converted into VII via conversion into a halo compound (Scheme C), an activated ester (Scheme C) or acid catalysis (Scheme A). In the first case, treatment of the hydroxy compound with hydrochloric, hydrobromic, hydriodic or hydrofluoric acid, preferably at reflux temperatures, converts it into the corresponding halo compound. Displacement of the halogen ($SN_2$) with a mercaptan under basic conditions (see above) provides compound IX.

The alcohols III or XI may be converted into activated esters such as those of toluene sulfonic acid (tosylates), methane sulfonic acid (mesylates), trifluoromethane sulfonic acid Triflates) and trifluoroacetic acid. Displacement of the activated ester ($SN_2$) with a mercaptan under basic conditions (see above) provides compound IX. Both this method and that outlined above utilizing a halo intermediate have the advantage that the stereochemistry at the carbon bearing the functional group may be inverted thus allowing control (selection) of the stereochemistry (cis or trans) of the product Treatment of alcohols III or XI with a mercaptan in the presence of an acid (Scheme A, B, C) should provide the corresponding sulfide, e.g., VII or XIII. Mineral acids, organic acids and Lewis acids are suitable for this reaction. Non-nucleophilic acids are preferred and include, for example, trifluoroacetic acid, toluene sulfonic acid, perfluorobutyric acid, triflic acid, phosphoric acid, sulfuric acid, boron trifluoride, aluminum chloride and the like.

Conversion of a carboxylic acid such as VII, XI or XII into an ester or an amide is accomplished by standard means. The carboxylic acid may be treated with the appropriate alcohol with or without added solvent in the presence of an acid (see above) to provide the product ester. A salt of the carboxylic acid may be prepared by treatment with a base (see above) and the salt then treated with an electrophilic group with displacement of, for example, a halide, tosylate and the like. An alternative method of preparation is conversion of the carboxylic acid into an activate carbonyl function such as an acid halide, mixed anhydride or activated ester followed by treatment with an appropriate alcohol or amine. Acid halides can be made by mixing, for example, thionyl chloride, thionyl bromide, phosphorus trichloride, phosphorus pentabromide, oxalyl chloride and the like with the acid. Mixed anhydrides with, e.g., isobutyl chloroformate, are prepared in the standard manner with the acid being treated with isobutyl chloroformate in the presence of a base or from a preformed carboxylate salt. The same type of salt, either prepared in the reaction or preformed, can be treated with for example, N-chlorosuccinimide, to form the succinimide activated ester. Treatment of either of these intermediates with the appropriate amine, alcohol, mercaptan or electrophile will provide the compounds of this invention.

The conversion of the alcohols/mercaptans III, XI, XVI, XVII and the like into compounds of, for example, X, is accomplished in the same manner as the synthesis of the other esters outlined above. In this case, the appropriate alcohol/mercaptan is represented as outlined above and the acylating agent is an acid halide or anhydride.

Scheme C illustrates yet another method for the preparation of the intermediates and compounds of this invention. An alpha-halo ketone, substituted or unsubstituted, is treated with a oxygen or sulfur nucleophile generated as described above. The valuable intermediate, XV, is reduced directly with, for example, a hydride reducing agent such as sodium borohydride, lithium aluminum hydride, sodium cyano borohydride and the like or borane, to provide the alcohols III and XI. The use of these intermediates for the preparation of compounds VII, VIII, XIV and X is discussed above. Conversion of ketone XV into a thioketone is readily accomplished using reagents such as phosphorus pentasulfide or 2,4-bis(4-methoxyphenyl)-1,3-dithia-2,4-diphosphetane-2,4-disulfide (Lawesson's Reagent). Reduction of the thioketone as discussed above for the ketones provides the mercaptan analogs of III and XI and it is used similarly.

SCHEME A

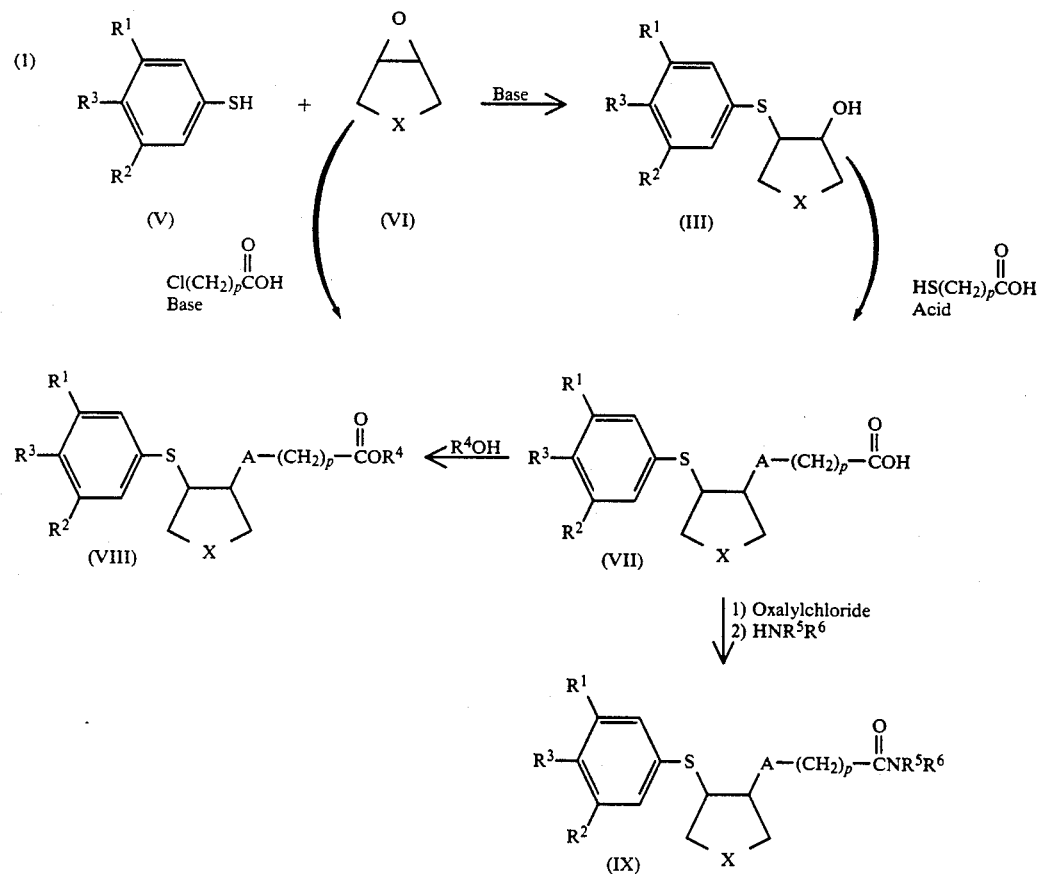

-continued
SCHEME A
(2) (III) $\xrightarrow{(RCO)_2O}$ 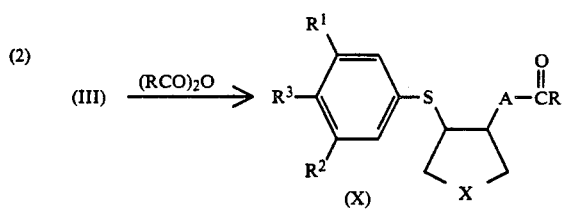
R = alkyl or $(CH_2)_rCOOR^7$
SCHEME B
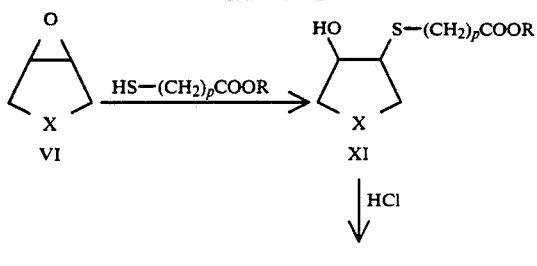
-continued
SCHEME B
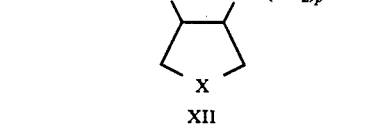
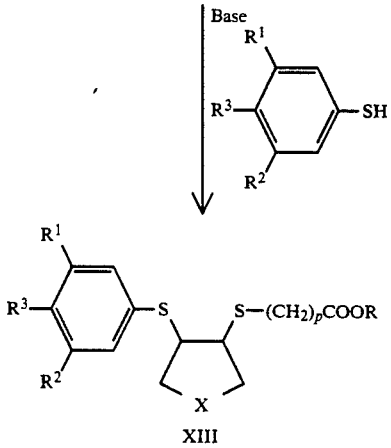
SCHEME C
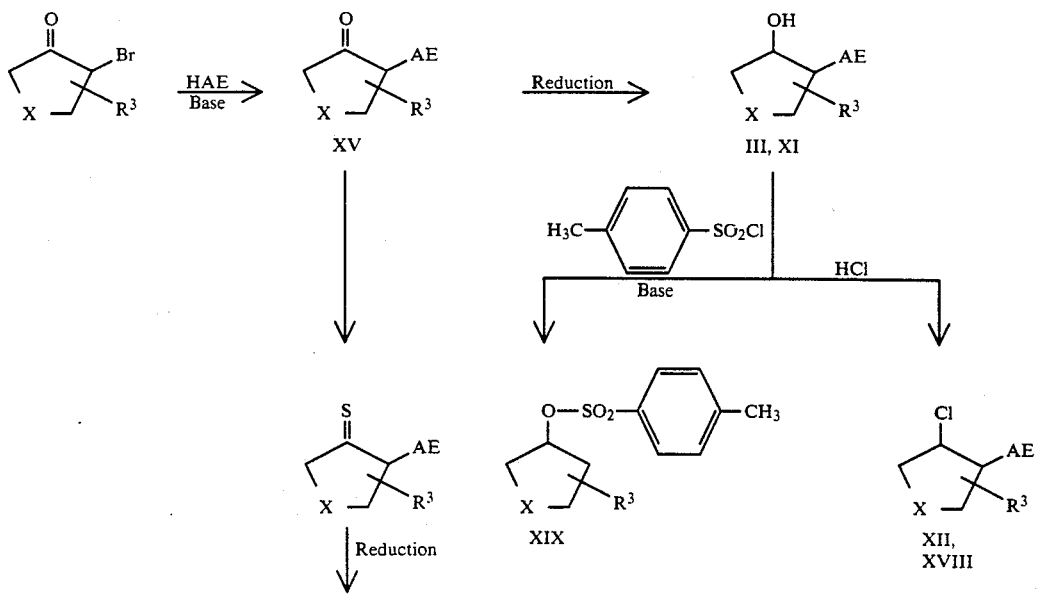

-continued
SCHEME C

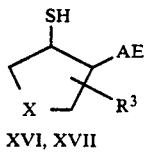

XVI, XVII

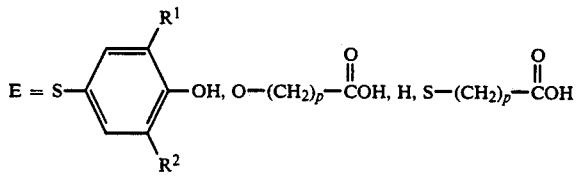

$R^3$ = alkyl

BIOLOGICAL EVALUATIONS

The compounds of the invention are evaluated with respect to 5-lipoxygenase inhibition according to the following assay procedure.

Inhibition of 5-lipoxygenase, in vitro:anti-inflammatory, anti-allergy activities.

The 100,000×g supernatant fraction of Rat Basophilic Leukemia Cell Homogenate (RBL-1) serves as a 5-lipoxygenase enzyme source. The enzyme is incubated with [i-$^{14}$C]-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The compounds of the invention are evaluated with respect to superoxide modulating activity according to the following assay procedure:

Human Neutrophil Superoxide Generation

Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. Biol. Chem.* 256: 12640–12643, 1981.) To 5 million neutrophils in 2.85 ml of Krebs-Ringer phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading minus the initial reading (before addition of FMLP) was used to calculate nanomoles of superoxide generated based on a molar extinction coefficient of $2.1 \times 10^4$ cm$^{-1}$mole$^{-1}$.

Isolation of Human Neutroohils

Human neutrophils were isolated from freshly drawn blood of healthy donors. Two ml of 5% dextran (MW 200,000–300,000) in saline was added to 10 ml aliquots of blood, mixed and placed upright for 45 min. at 37° C. Approx. 8–10 ml of the plasma-white cell suspension from the dextran sedimentation was layered on 3 ml of Ficol-paque in a 15 ml tube and centrifuged at 400 g for 30 min. The supernate, containing plasma and platelets, was discarded by aspiration, and the pellet, containing predominantly neutrophils, was resuspended in 1 ml saline. The suspension was transferred to a clean tube, and pooled with other aliquots of blood treated similarly. The pooled suspension was centrifuged at 350 g for 5 min. and supernate discarded. The pellet was resuspended in 5 ml of 0.05% NaCl with a plastic Pasteur pipette for 25 seconds to lyse contaminating red cells, then 5 ml of 1.75% NaCl added to regain isotonicity. The red cell lysing procedure was repeated, the cells suspended in appropriate buffer (depending on assay) and counted.

For comparison the compound of Formula XX, a known 5-lipoxygenase inhibitor described in U.S. Pat. No. 4,755,524 was used.

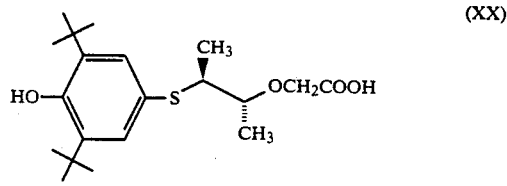

(XX)

(±)[2S*-[[3,5-Bis(1,1-dimethylethyl)-4-hydroxyphenyl]thio]-1R*-methylpropoxy]acetic acid The results with respect to certain compounds of the present invention are set forth in Table I below.

TABLE 1

| Compound Example Number | 5-Lipoxygenase Inhibition IC$_{50}$ (μM) | FMLP Induced Superoxide Generation |
|---|---|---|
| 16 | 1.1 | Inhibition IC$_{50}$ = 3 μM |
| 20 | 2.1 | Inhibition IC$_{50}$ = 5 μM |
| 31 | 0.18 | Stimulation 10 μM, 67% > control 25 μM, 100% > control 50 μM, 133% > control |
| Formula XX | 4.9 | Inhibition IC$_{50}$ = 11 μM |

The compound of Formula XX inhibited both superoxide generation and 5-lipoxygenase whereas the compound of Example 31 inhibited 5-lipoxygenase an stimulated superoxide generation. This data indicates that superoxide generation is not dependent on 5-lipoxygenase and that the ability of a compound to inhibit 5-lipoxygenase is not related to its ability to simulate superoxide generation.

Complement C5a induced superoxide generation may also be stimulated or inhibited by compounds of the present invention.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

The following non-limiting examples further illustrate details for the preparation of the compounds of the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

EXAMPLE 1

3,6-Dioxabicyclo[3.1.0]hexane

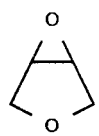

2,5-Dihydrofuran (DHF) (13.2 g, 0.188 mole) was added by syringe to a solution containing 3-chloroperoxybenzoic acid (29.1 g, 0.198, mole) and trifluorocetic acid (0.5 ml) in methylene chloride (500 ml). After stirring at room temperature for 20 hours, the white solid was removed by filtration. The filtrate was washed with a solution of sodium carbonate (100 ml, saturated). The organic phase was stirred with solid sodium carbonate and sodium thiosulfate for 20 minutes and filtered. The product was purified by low pressure distillation (41° C./5 mmHg). The structure was supported by NMR.

EXAMPLE 2 trans-4-[[3,5-bis(1,1-Dimethylethyl)-4-hydroxyphenyl]-thio]tetrahydro-3-furanol

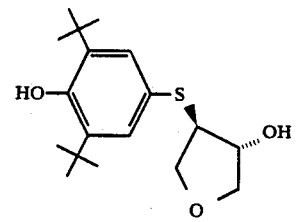

2,6-bis(1,1-Dimethylethyl)-4-mercaptophenol (1.85 g, 0.0078 mole) and the compound of Example 1 (0.64 g, 0.0074 mole) were added to a degassed (Argon) solution of 50% sodium hydroxide (5 ml) and isopropyl alcohol (50 ml). The reaction was heated to reflux for 24 hours. The reaction was cooled to room temperature and poured into water (125 ml). The solution was made acidic with 1N hydrochloric acid and extracted 3 times with 100 ml of diethyl ether. The combined diethyl ether extracts were dried over anhydrous magnesium sulfate, filtered and concentrated to an oily solid in a rotary evaporator. The product was purified by silica gel chromatography and recrystallized from hexane (m.p. ca. 104° C.). The structure was supported by NMR and infrared spectroscopy and elemental analysis.

Analysis calculated for: $C_{18}H_{27}SO_3$ (m.w.=323.47): Theory: C, 66.84; H, 8.41; S, 9.91. Found: C, 66.56; H, 8.52; S, 10.10.

EXAMPLE 3 trans-[(2-Hydroxycyclopentyl)thio]acetic acid

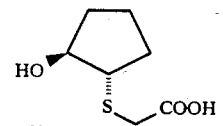

Mercaptoacetic acid (22.5g 0.244 mole) was added to a cold (+5° C.) solution of sodium methoxide [prepared from sodium (11.2 g, 0.488 mole)] in methanol (125 ml). After stirring for 20 minutes, cyclopentene oxide (19.5 g, 0.23 mole) was added dropwise over 20 minutes to the cold solution. The ice bath was removed and the reaction was refluxed for 45 minutes. The reaction was cooled to room temperature and made acidic by the addition of 4N hydrochloric acid. Water (100 ml) was added and the mixture was extracted twice with 150 ml of diethyl ether. The combined diethyl ether extracts were washed with water (50 ml), dried over anhydrous magnesium sulfate, filtered and concentrated to an oil with a rotary evaporator. The structure was confirmed by NMR spectroscopy.

EXAMPLE 4 trans[(2-Chlorocyclopentyl)thio]acetic acid

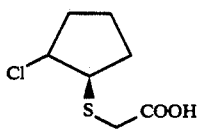

Concentrated hydrochloric acid (50 ml) was added to the product of Example 3 (8.4 g) and stirred for 20 hours at room temperature. The reaction mixture was poured into a solution of water (50 ml) containing sodium chloride and extracted three times with 75 ml of diethyl ether. The combined diethyl ether extracts were dried over anhydrous magnesium sulfate, filtered and concentrated to an oil with a rotary evaporator. The product was purified by silica gel chromatography, and the structure was supported by NMR spectroscopy. The NMR spectrum showed a small amount of the cis- product as well.

EXAMPLE 5 trans-[[2-[[3,5-bis(1,1-Dimethylethyl)-4-hydroxyphenyl]thio]cyclopentyl]thio]acetic acid

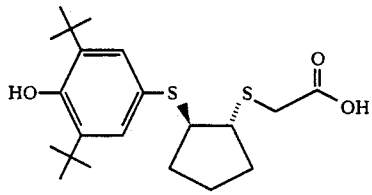

2.6-bis(1,1-Dimethylethyl)-4-mercaptophenol (0.73 g, 0.0031 mole) was added to freshly prepared sodium ethoxide [sodium (0.16 g, 0.007 mole)] in ethanol (10 ml). Once dissolved, the product of Example 4 (0.50 g, 0.0026 mole) was added and the reaction mixture was stirred for 90 minutes and poured into water (50 ml) containing 1N hydrochloric acid (25 ml). The mixture was extracted three times with 20 ml of diethyl ether, and the combined extracts were washed with water (20 ml), dried over anhydrous magnesium sulfate, filtered and concentrated to an oil with a rotary evaporator. The product was purified by silica gel chromatography. The structure was supported by NMR and elemental analysis.

Analysis calculated for: $C_{21}H_{32}S_2O_3$ (m.w.=396.61): Theory: C, 63.60; H, 8.13; S, 16.17. Found: C, 63.69; H, 8.40; S, 15.83.

EXAMPLE 6

Methyl trans-[[2-[[3,5-bis(1,1-dimethylethyl)-4-hydroxyphenyl]thio]cyclopentyl]thio]acetate

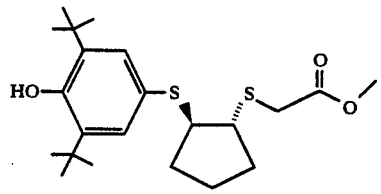

The compound of Example 5 (1.0 g, 0.0025 mole) was dissolved in methanol (35 ml) and hydrogen chloride gas was bubbled into the solution for 10 minutes. Nitrogen gas was bubbled into the reaction solution to remove most of the dissolved hydrogen chloride, and then the reaction mixture was poured into water (150 ml). The mixture was extracted twice with 100 ml of diethyl ether, and the combined extracts were dried over anhydrous magnesium sulfate, filtered and concentrated to an oil with a rotary evaporator. The product was purified by silica gel chromatography. The structure was supported by NMR, infrared spectroscopy and elemental analysis.

Analysis calculated: for $C_{22}H_{34}S_2O_3$ (m.w.=410.92): Theory: C, 64.35; H, 8.35; S, 15.62. Found: C, 64.49; H, 8.30; S, 15.86.

EXAMPLE 7 trans-2,6-bis(1,1-Dimethylethyl)-4-[(2-hydroxycyclopentyl)thio]phenol

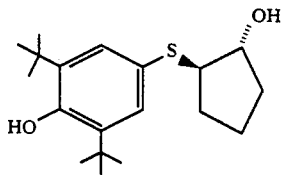

2.6-bis(1,1-Dimethylethyl-4- mercaptophenol (11.5 g, 0.048 mole) was added to a solution of sodium methoxide [prepared from sodium (2.2 g, 0.097 mole)] in methanol (75 ml). After several minutes, cyclopentene oxide (3.86 g, 0.046 mole) was added, and the reaction mixture was stirred at room temperature for 20 hours. The reaction mixture was poured into water (100 ml) containing saturated brine (50 ml) and 1N hydrochloric acid (80 ml). The mixture was extracted twice with 100 ml of diethyl ether. The combined diethyl ether extracts were dried over anhydrous magnesium sulfate, filtered and concentrated to an oil with a rotary evaporator. The product was purified by silica gel chromatography to give the product as a white solid which was recrystallized from hexane (DSC.m.p. 90° C.). The structure was supported by NMR and elemental analysis.

Analysis calculated for: $C_{19}H_{30}SO_2$ (m.w.=322.50): Theory: C, 70.76; H, 9.38; S, 9.94. Found: C, 71.14; H, 9.64; S, 10.02.

EXAMPLE 8

Methyl trans-[[2-[[3,5-bis(1,1-dimethylethyl)-4-hydroxyphenyl]thio]cyclopentyl]thio]acetate

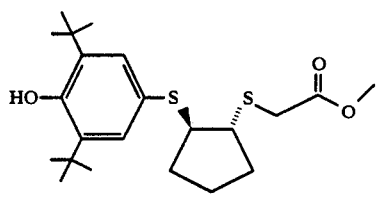

The compound of Example 7 (5.0 g, 0.0155 mole) was added to trifluoroacetic acid (20 ml). After several minutes methyl thioglycolate (1.80 g, 0.0170 mole) was added, and the reaction mixture was stirred for 1.5 hours at room temperature. The trifluoroacetic acid was removed by evaporation with a gentle flow of nitrogen gas. The residue was dissolved in diethyl ether (100 ml), washed four times with 50 ml of 0.3N hydrochloric acid and once with 25 ml of water, dried over anhydrous magnesium sulfate, filtered and concentrated to an oil with a rotary evaporator to give the product as an oil. The structure was supported by NMR and was shown by thin layer chromatography to be identical to the compound prepared in Example 6.

EXAMPLE 9 trans-[[2-[[3,5-bis(1,1-Dimethylethyl)-4-hydroxyphenyl]thio]cyclopentyl]thio]acetic acid

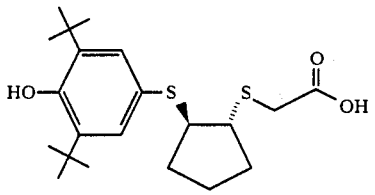

Lithium hydroxide hydrate (1.0 g, 0.025 mole) was added to a solution of the compound of Example 8 (4.13 g, 0.010 mole) in methanol (40 ml). Water (20 ml) was added over 10 minutes to the reaction mixture. 1.0N hydrochloric acid (25 ml) was added slowly to the reaction mixture followed by water (50 ml) and brine (50 ml). The mixture was extracted twice with 75 ml of diethyl ether. The combined diethyl ether extracts were washed with brine (25 ml), dried over anhydrous magnesium sulfate, filtered and concentrated to an oil by a gentle flow of nitrogen gas. The product was purified by silica gel chromatography. The structure was supported by NMR, infrared spectroscopy and elemental analysis.

Analysis calculated: for $C_{21}H_{32}S_2O_3$ (m.w.=396.61): Theory: C, 63.60; H, 8.13; S, 16.17. Found: C, 63.52; H, 8.02; S, 16.15.

EXAMPLE 10 trans-[(2-Hydroxycyclohexyl)thio]acetic acid

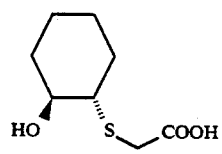

Mercaptoacetic acid (18.5 g), 0.20 mole) was added to methanol (125 ml) containing sodium methoxide [prepared from sodium (9.3 g, 0.40 mole)] cooled by an ice bath. After 20 minutes, cyclohexene oxide was added slowly during 20 minutes. The ice bath was removed, and the reaction mixture was stirred at room temperature for 4 hours at which time it was poured into water (250 ml) containing concentrated hydrochloric acid (50 ml) and brine (200 ml). The reaction mixture was extracted three times with 150 ml of diethyl ether. The combined diethyl ether extracts were washed twice with 50 ml of brine, dried over anhydrous magnesium sulfate, filtered and concentrated with a rotary evaporator to give the product as an oil. The structure was supported by NMR.

EXAMPLE 11

[(2-Chlorocyclohexyl)thio]acetic acid

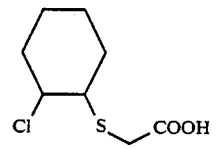

Concentrated hydrochloric acid (200 ml) was added to the compound of Example 10 (27.1 g, 0.13 mole) and the reaction mixture was stirred at room temperature for 20 hours. Water (100 ml) and brine (50 ml) were added to the reaction mixture. The reaction mixture was extracted three times with 175 ml of diethyl ether. The combined diethyl ether extracts were washed three times with 30 ml of water and dried over anhydrous magnesium sulfate, filtered and concentrated to an oil with a rotary evaporator. The product was purified by silica gel chromatography. The structure was supported by NMR.

EXAMPLE 12

Methyl [(2-chlorocyclohexyl)thio]acetate

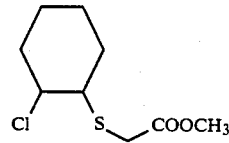

Starting with the compound of Example 11 and using the method of Example 6 the product was obtained. The title compound, methyl [(2-chlorocyclohexyl)thio]acetate, was isolated by silica gel chromatography. The structure was supported by NMR.

EXAMPLE 13

4-[(2-Chlorocyclopentyl)thio]-2,6-bis(1,1-dimethylethyl)phenol

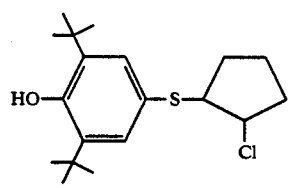

The product of Example 7 (0.40 g, 0.0012 mole) was stirred with concentrated hydrochloric acid (5 ml) at room temperature for 20 hours. The solid was removed by filtration, washed with water and air dried to give the product as a white powder. The product was purified by silica gel chromatography to give a white solid. The structure was supported by NMR.

EXAMPLE 14

4-[(2-Chlorocyclohexyl)thio]-2,6-bis(1,1-dimethylethyl)phenol

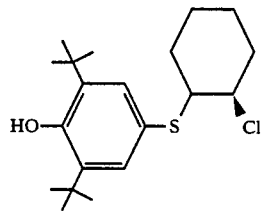

Starting with trans-2,6-bis(1,1-dimethylethyl)-4-[(2-hydroxycyclohexyl)thio]phenol (Example 15) and using the method described in Example 13, the title compound was obtained.

EXAMPLE 15 trans-2,6-bis(1,1-Dimethylethyl)-4-[(2-hydroxycyclohexyl)thio]phenol

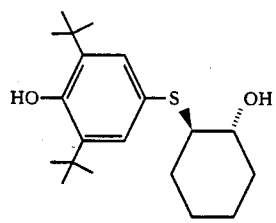

2,6-bis(1,1-Dimethylethyl)-4-mercaptophenol (12.8 g, 0.054 moles) was added to a solution of sodium ethoxide [prepared from sodium (2.5 g 0.108 mole)] in ethyl alcohol (75 ml). Cyclohexene oxide (5.15 g, 0.0525 mole) was added and the reaction mixture was stirred at room temperature for 20 hours. The reaction mixture was poured into 10% hydrochloric acid (250 ml) and the mixture was extracted twice with 200ml of ethyl ether. The combined ethyl ether extracts were washed twice with 25 ml of water, dried over magnesium sulfate, filtered and concentrated in vacuo to a yellow oil. The product was purified by silica gel chromatography and recrystallized from methyl alcohol/water, m.p. ca 91° C. The structure was supported by NMR, infrared spectroscopy, and elemental analysis.

Analysis calculated for: $C_{20}H_{32}SO_2$ (m.w.=336.54): Theory: C, 71.38; H, 9.58; S, 9.52. Found: C, 71.35; H, 9.66; S, 9.56.

EXAMPLE 16 trans-[[2-[[3,5-bis(1,1-Dimethylethyl)-4-hydroxyphenyl]thio]cyclohexyl]thio]acetic acid

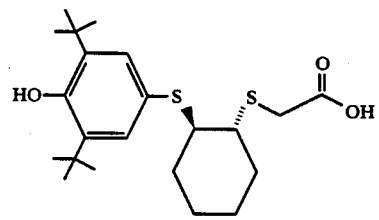

Methyl thioglycolate (4.8 g, 0.0448 mole) was added to a solution of the compound of Example 15 (15.0 g, 0.0448 moles) in methylene chloride (20 ml). After stirring for 15 minutes, trifluoroacetic acid (18 ml) was added to the reaction mixture. The reaction mixture was stirred for 64 hours and then poured into methyl alcohol (100 ml) containing potassium hydroxide (13g, 0.23 moles) and lithium hydroxide hydrate (9.7 g, 0.23 moles). Over the next 3 hours water was added to bring the final volume to 300 ml. The solution was washed twice with 150 ml of ethyl acetate. The aqueous layer was made acidic to pH 2 with concentrated hydrochloric acid. The reaction mixture was extracted twice with 200 ml of ethyl acetate. The combined ethyl acetate extracts were dried over sodium sulfate, filtered and concentrated in vacuo to give the product as an oil. The product was purified by silica gel chromatography. The resulting oil was heated at 65° C. under vacuum to remove a trace amount of ethyl acetate. The structure assignment was supported by NMR, infrared spectroscopy, and elemental analysis.

Analysis calculated for: $C_{22}H_{34}O_3S_2$ (m.w.=410.6): Theory: C, 64.35; H, 8.34; S, 15.62. Found: C, 64.22; H, 8.27; S, 15.41.

EXAMPLE 17

Methyl trans-[[2-[[3,5-bis(1,1-dimethylethyl)-4-hydroxyphenyl]thio]cyclohexyl]thio]acetate

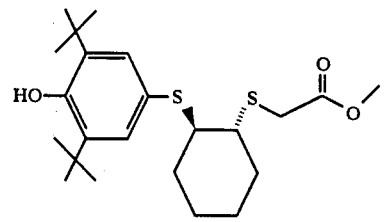

The compound of Example 15 (2.0 g, 0.0059) was added to trifluoroacetic acid (5 ml). After several minutes methyl thioglycolate (0.63 g) was added, and the reaction mixture was stirred at room temperature for 2 hours. The trifluoroacetic acid was evaporated with a gentle flow of nitrogen gas. The residue was dissolved in diethyl ether (50 ml) and washed twice with 2 ml of 0.25 N NaOH, dried over anhydrous magnesium sulfate, filtered and concentrated to an oil. The product was purified by silica gel chromatography to give a colorless oil. The structure was supported by NMR, infrared and elemental analysis.

Analysis calculated for: $C_{23}H_{36}S_2O_3$ (m.w.=424.66): Theory: C, 65.05; H, 8.54; S, 15.10. Found: C, 65.08; H, 8.41; S, 15.30.

EXAMPLE 18 trans-4-[[3,5-bis(1,1-Dimethylethyl)-4-hydroxyphenyl]-thio]tetrahydro-3-furanol, acetate

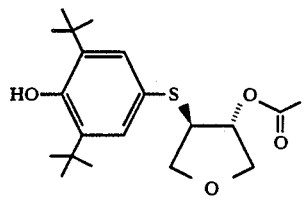

The compound of Example 2 (2.0 g, 0.0062 mole) was added to acetic anhydride (20ml). Triethylamine (0.62 g, 0.0062 mole) was added, and the reaction mixture was stirred for 3 hours. Additional triethylamine (0.3 ml) was added, and the reaction mixture was stirred for 2 hours. The reaction mixture was concentrated to an oil with a gentle flow of nitrogen gas. The residue was dissolved in diethyl ether (75 ml), washed twice with 50ml of 0.25N hydrochloric acid and once with 25 ml of brine, dried over anhydrous magnesium sulfate, filtered and concentrated with a gentle flow of nitrogen gas. The product was purified by silica gel chromatography and crystallized from hexane (DSC m.p. ca, 72° C.). The structure was supported by NMR, infrared spectroscopy and elemental analysis.

Elemental analysis calculated for: $C_{20}H_{30}SO_4$ (m.w.=366.51): Theory: C, 65.54; H, 8.25; S, 8.75. Found: C, 65.52; H, 8.31; S, 8.84.

EXAMPLE 19

Butanedioic acid, trans-mono[4-[[3,5-bis(1,1-dimethylethyl) 4-hydroxyphenyl]thio]tetrahydro-3-furanyl]ester

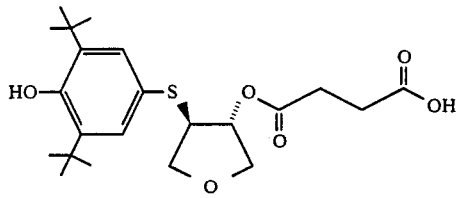

Succinic anhydride (1.85, 0.0185 mole) and triethylamine (1.87 g, 0.0185 mole) were added to a solution of tetrahydrofuran (THF) (50 ml) containing the compound of Example 2 (3.0 g, 0.0092 mole). The reaction mixture was stirred for 3 days and then concentrated to an oil with a gentle flow of nitrogen gas. The residue was dissolved in diethyl ether. The solution was washed twice with 50 ml of water and once with 20 ml of 1N hydrochloric acid, dried over anhydrous magnesium sulfate, filtered and concentrated to an oil with a rotary evaporator. The product was purified by silica gel chromatography to give a solid which was recrystallized from diethyl ether/hexane (DSC m.p. ca, 112° C.). The structure was supported by NMR, infrared spectroscopy and elemental analysis.

Analysis calculated for: $C_{22}H_{32}SO_6$ (m.w.=424.60): Theory: C, 62.23; H,7.61; S,7.55. Found: C, 62.63; H, 7.53, S, 7.67.

EXAMPLE 20 trans-[[2-[[3,5-bis(1,1-Dimethylethyl)-4-hydroxyphenyl]thio]cyclohexyl]oxy]acetic acid

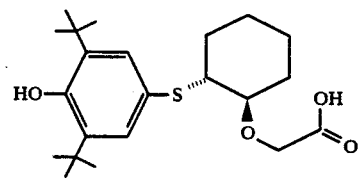

trans-2,6-bis(1,1-Dimethylethyl)-4-[(2-hydroxycyclohexyl)thiophenol (6.73 g, 0.020 mole) was added in portions to a mixture of sodium hydride (1.49 g, 0.062 mole) in dimethylsulfoxide (50 ml) while cooling with an ice bath. After stirring the reaction mixture for 1 hour at room temperature, chloroacetic acid, sodium salt (2.56 g, 0.022 mole) was added, and the reaction mixture was stirred for 20 hours. After cooling the reaction mixture to 5° C. with an ice bath, 10% hydrochloric acid (10 ml) was added slowly. The reaction mixture was then poured into water (100 ml) and extracted with ethyl acetate-hexane (50 ml-50 ml). The organic layer was washed with brine (100 ml), dried over anhydrous sodium sulfate, filtered and concentrated to an orange oil in a rotary evaporator. The product was purified by silica gel chromatography and recrystallized for ethyl acetate-hexane (DSC m.p. ca. 124° C.). The structure was supported by NMR, infrared spectroscopy and elemental analysis.

Analysis calculated for: $C_{22}H_{34}SO_4$ (m.w.=394.57): Theory: C, 66.97; H, 8.68; S, 8.12. Found: C, 67.31; H, 8.95; S, 7.79.

EXAMPLE 21 trans-[[4-[[3,5-bis(1,1Dimethylethyl)-4-hydroxyphenyl]thio]tetrahydro-3-furanyl]oxy]acetic acid

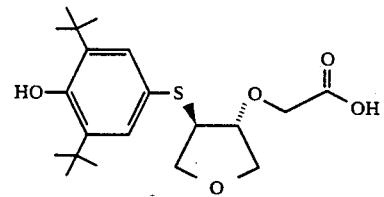

The compound of Example 2 (3.6 g, 0.011 mole) and chloroacetic acid (2.04 g, 0.022 mole) were added to t-butyl alcohol (40 ml) to which had been added potassium (1.39 g, 0.033 mole) and the reaction mixture was refluxed for 36 hours. The reaction mixture was cooled to room temperature, and 1N hydrochloric acid (50 ml) was added slowly. The reaction mixture was extracted twice with 100 ml of diethyl ether. The combined diethyl ether extracts were washed with saturated sodium bicarbonate (2×100 ml), 1N hydrochloric acid (10 ml) and brine (20 ml) dried over anhydrous sodium sulfate, filtered and concentrated in a rotary evaporator to give the crude product as an oil. The product was purified by silica gel chromatography and recrystallized from ethyl acetate-hexane. The structure was supported by NMR and infrared spectroscopy and elemental analysis.

Analysis calculated for: $C_{20}H_{30}SO_5$ (m.w.=382.56): Theory: C, 62.80; H, 7.90. Found: C, 62.69; H, 7.92.

EXAMPLE 22

3,5-bis(1,1-Dimethylethyl)-4-hydroxyphenyl thiocyanate

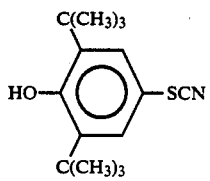

To a three-necked, round bottom 5 L flask, equipped with a mechanical stirrer, gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1 and ½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated by addition of water, filtered and dried for 2 days over phosphorous pentoxide. The resulting gummy yellow solid was recrystallized from pentane and dried in vacuo to yield the product as a white powder, m.p. 61.5°-63° C.

Analysis calculated for: $C_{15}H_{21}NSO$: Theory: C, 68.40; H, 8.03; N, 5.32; S, 12.17. Found: C, 68.85; H, 8.05; N, 5.29; S, 12.12.

EXAMPLE 23

2,6-bis(1,1-Dimethylethyl)-4-mercaptophenol

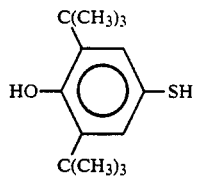

3,50-bis(1,1-Dimethylethyl)-4-hydroxyphenyl thiocyanate (55 g, 0.209 mole) .was dissolved in acetone (200 ml) under an argon atmosphere. Water (7.6 g, 0.42 mole) was added, and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, and the solvents were removed to yield a white powder which was recrystallized from methanol/water and dried to yield 43.3 g of the desired product. NMR confirmed the identity of the product.

EXAMPLE 24

Methyl [(2-chlorocyclohexyl)sulfinyl]acetate

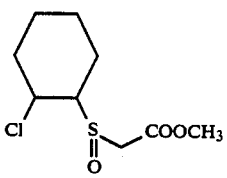

Methyl [(2-chlorocyclohexyl)thio]acetate (2.5 g, 0.0112 mole) was added to methylene chloride (35 ml) and the mixture was cooled to 5° C. with an ice bath. 3-Chloroperoxybenzoic acid (85%, 2.3 g, 0.0112 mole) was added, and the reaction mixture was stirred at room temperature for 20 hours. The reaction mixture was cooled to 5° C. with an ice bath, and filtered. Solid sodium thiosulfate was added to the filtrate and the mixture was stirred for several minutes then filtered. The filtrate was dried over anhydrous magnesium sulfate. After filtering, the filtrate was concentrated in a rotary evaporator to give the product as a solid. The structure was supported by NMR.

EXAMPLE 25

Methyl [(2-chlorocyclohexyl)sulfonyl]acetate

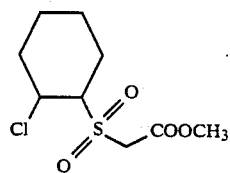

The compound of Example 24 (3.5 g, 0.0112 mole) was dissolved in methylene chloride and cooled to 5° C. with an ice bath. 3-Chloroperoxybenzoic acid (85%, 2.3 g 0.0112 mole) was added, and the reaction mixture was stirred at room temperature for 4 hours. The reaction mixture was filtered and concentrated in a rotary evaporator to give the crude product as a solid. The product was purified by silica gel chromatography. The structure was supported by NMR.

EXAMPLE 26

Methyl [[2-[[3,5-bis(1,1-dimethylethyl)-4-hydroxyphenyl]thio]-cyclohexyl]sulfonyl]acetate

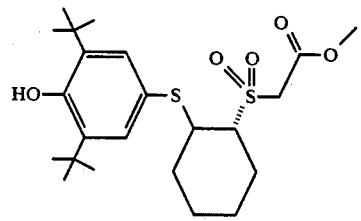

2,6-bis(1,1-Dimethylethyl)-4-mercaptophenol (3.2 g, 0.013 mole) was added to a solution of methyl [(2-chlorocyclohexyl)sulfonyl]acetate (0.85 g, 0.0033 mole) in triethylamine (13 ml) and the reaction mixture was refluxed for 5 hours. The reaction mixture was cooled to room temperature and poured into 1N hydrochloric acid (150 ml). The mixture was extracted twice with 50 ml of diethyl ether, then washed twice with 20 ml of 1.5N hydrochloric acid and once with brine (10 ml), dried over anhydrous magnesium sulfate, filtered and concentrated in a rotary evaporator to give the crude product as an oil. The product was purified by silica gel chromatography to give a solid m.p. ca. 105° C. The structure was supported by NMR, and infrared spectroscopy and elemental analysis.

Analysis calculated for: $C_{23}H_{36}S_2O_5$ (m.w.=456.71): Theory: C, 60.49; H, 7.95; S, 14.04. Found: C, 60.66; H, 8.35; S, 13.96.

EXAMPLE 27

Methyl [[2-[[3,5-bis(1,1-dimethylethyl)-4-hydroxyphenyl]thio]-cyclohexyl]sulfonyl]acetate

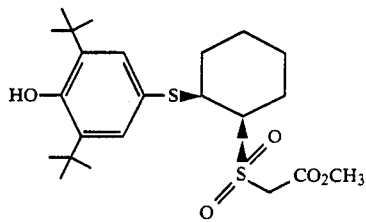

The titled compound was isolated as a product from the reaction mixture of Example 26 by silica gel chromatography (m.p. ca 93° C.). The structure was supported by NMR, infrared spectroscopy and elemental analysis.

Analysis calculated for: $C_{23}H_{36}O_5S_2$ (m.w.=456.71): Theory: C, 60.49; H, 7.95; S, 14.04. Found: C, 60.78; H, 8.22; S, 14.18.

EXAMPLE 28

Methyl [(2-chlorocyclopentyl)thio]acetate

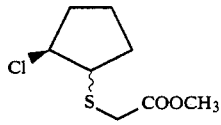

trans-[(2-Chlorocyclopentyl)thio]acetic acid was dissolved in methanol (35 ml) and the solution was cooled to 5° C. with an ice bath. Hydrogen chloride gas was bubbled into the solution for 15 minutes. The methanol was removed with a gentle flush of nitrogen gas. The residue was dissolved in diethyl ether (50 ml) and washed twice with 50 ml of 15% sodium hydroxide, dried over anhydrous magnesium sulfate, filtered and concentrated to give the product as an oil. The structure was supported by NMR.

EXAMPLE 29

Methyl [(2-chlorocyclopentyl)sulfonyl]acetate

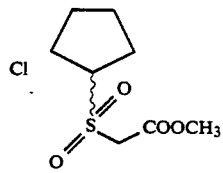

meta-Chloroperoxybenzoic acid (82%, 5.08 g, 0.024 mole) was added to a cold (5° C.) solution of methyl [(2-chlorocyclopentyl)thio]acetate (2.50 g, 0.0120 mole) in methylene chloride (45 ml) and the reaction mixture was stirred for 3 hours at room temperature. The reaction mixture was filtered and sodium thiosulfate was added to the filtrate with stirring. After several minutes the reaction mixture was filtered and the filtrate was concentrated to a semisolid in a rotary evaporator. The crude product was purified by silica gel chromatography to give the title compound. The structure was supported by NMR and infrared spectroscopy.

EXAMPLE 30

(a) Methyl trans-[[2-[[3,5-bis(1,1-dimethylethyl)-4-hydroxyphenyl]thio]cyclopentyl]sulfonyl]acetate (b) Methyl cis-[[2-[[3,5-bis(1,1-dimethylethyl)-4-hydroxyphenyl]thio]cyclopentyl]sulfonyl]acetate

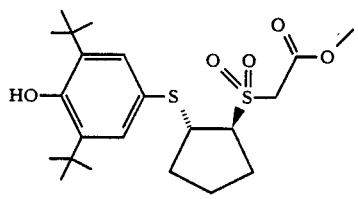

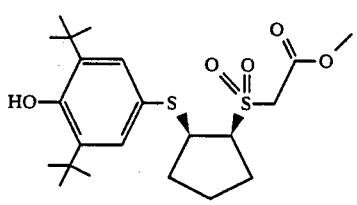

Starting with methyl [(2-chlorocyclopentyl)sulfonyl]acetate and following the procedure of Example 26 gave the title compound. The compounds were purified and separated by silica gel chromatography. The structures were supported by NMR.

EXAMPLE 31 trans-2-[[2-[[3,5-bis(1,1-Dimethylethyl)-4-hydroxyphenyl]thio]cyclohexyl]thio]-N-methyl-N-(2-pyridinylethyl)acetamide

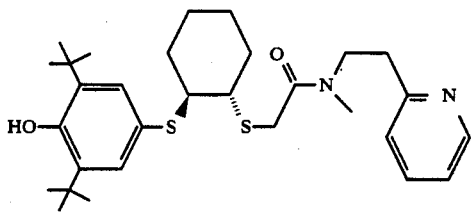

Oxalyl chloride (0.13 g, 0.00105 moles) was added to a cold (10° C.) solution of trans-[[2-[[3,5-bis(1,1-dimethylethyl)-4-hydroxyphenyl]thio]cyclohexyl]thio]acetic acid (0.39 g, 0.00095 mole) in benzene (50 ml). The cold bath was removed and the reaction mixture was stirred at room temperature for 20 hours. The reaction mixture was concentrated in vacuo to an oil. The oil was dissolved in toluene (50 ml) and then concentrated once again. The process was repeated using tetrahydrofuran (25 ml) in place of toluene. To a solution of the oil in tetrahydrofuran (50 ml) was added 2-(2-methylaminoethyl) pyridine (0.13 g, 0.00095 moles) and triethylamine (1 ml) and the reaction mixture was stirred at room temperature for 44 hours. After removal of the while solid precipitate by filtration, the filtrate was concentrated to give the crude product as an oil. The product was purified by silica gel chromatography. The resulting oil was heated in vacuo at 100° C. for 3 hours to remove traces of solvent. The structure assignment was supported by NMR, infrared spectroscopy and elemental analysis.

Analysis calculated for: $C_{30}H_{44}N_2O_2S_2$ (m.w.=528.8): Theory: C, 68.14; H, 8.39; S, 5.30. Found: C, 68.19; H, 8.59; S, 5.25.

EXAMPLE 32 trans-2-[[2-[[3,5-Bis(1,1-dimethylethyl)phenyl]thio]cyclohexyl]thio]-N-methyl-N-(2-pyridinylethyl)acetamide

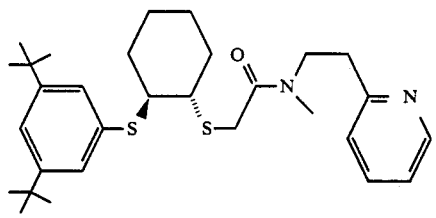

Oxalyl chloride (0.19 g, 0.0015 moles) was added by syringe to a cold (10° C.) solution of trans-[[2-[[3,5-bis(1,1-dimethylethyl)phenyl]thio]cyclohexyl]thio]acetic acid (0.55 g, 0.0014 moles) in benzene (50 ml). The cold bath was removed and the reaction mixture was stirred at room temperature for 20 hours. The reaction mixture was concentrated to an oil (rotary evaporator). The oil was dissolved in toluene (50 ml) and concentrated to an oil. The process was repeated using tetrahydrofuran (25 ml) instead of toluene. The residue was dissolved in tetrahydrofuran (50 ml). To this solution was added 2-(2-methylaminoethyl)pyridine (0.19 g, 0.0014 moles) and triethylamine (0.22 g) and the reaction mixture was stirred at room temperature for 48 hours. The white solid precipitate was removed by filtration and washed with ethyl acetate (25 ml). The filtrate was concentrated to give the crude product as an oil. The product was purified by silica gel chromatography and dried in vacuo at 100° C. for 1 hour to give the title compound. The structure assignment was supported by NMR, infrared spectroscopy and elemental analysis.

Analysis calculated for: $C_{30}H_{44}N_2OS_2$ (m.w.=512.83): Theory: C, 70.26; H, 8.65; S, 5.46. Found: C, 69.95; H, 8.76; S, 5.43.

EXAMPLE 33

2'-hydroxy[1,1':3',1''-terphenyl]-5'-yl thiocyanate

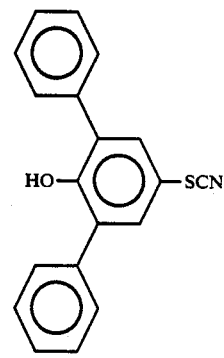

2,6-Diphenylphenol (100 g, 0.406 mole) and ammonium thiocyanate (67.99 g, 0.893 mole) were suspended in methanol (150 ml) in a three necked round bottom flask equipped with magnetic stirrer, thermometer and bubbler. The reaction mixture was cooled to −5° C. in an acetone/ice bath and chlorine gas was bubbled through the solution for three hours. Maintaining the temperature below 10° C., ammonia gas was bubbled through the reaction for 2 hours. The contents of the flask were then poured into iced distilled water (250 ml) and allowed to stand for 12 hours. After filtering, the solid was dried in vacuo at 45° C. for 12 hours. The title compound was purified by chromatography on silica and recrystallized from hexane, m.p. ca. 104°–106.5° C.

EXAMPLE 34

5''-mercapto-[1,1'':3''1Δ-terphenyl]-2'-ol

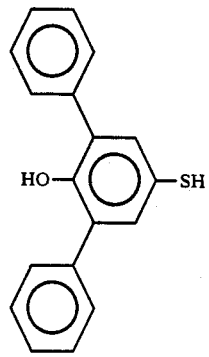

The title compound of Example 33 (32.2 g, 0.106 mole) and water (1.9 ml) were dissolved in acetone (150 ml) with stirring and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica.

Analysis calc. for $C_{18}H_{14}OS$ (278.31): Calc.: C, 77.67; H, 5.07; S, 11.52. Found: C, 77.80; H, 5.19; S, 11.68.

EXAMPLE 35 trans-[[2-[(2'-hydroxy[1,1':3',1''-terphenyl]-5'-yl)thio]cyclohexyl]thio]acetic acid

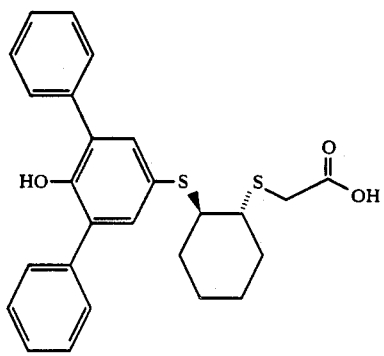

Starting with the compound of Example 34 and following the procedures described in Example 15 and 16 gives trans-[[2-[(2'-hydroxy[1,1':3',1''-terphenyl]-5'-yl)thio]cyclohexyl]thio]acetic acid.

EXAMPLE 36

The following compounds are made by substituting 5'-mercapto-[1,1':3',1''-terphenyl]-2'-ol (Example 34) for 2,6-bis-(1,1-dimethylethyl)-4-mercaptophenol (Example 23) in the following Examples and following the procedures described therein:

(a) Substituting in Example 5 and following the procedure therein gives trans-[[2-[(2'-hydroxy[1,1':3',1''-terphenyl]-5'-yl)thio]cyclopentyl]thio]acetic acid;

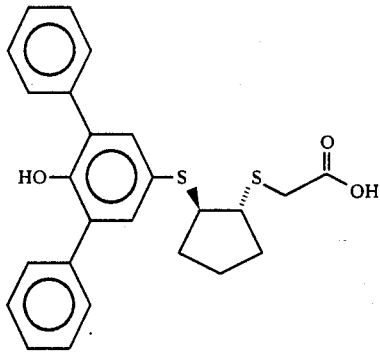

(b) Substituting in Example 31 and following the procedure therein gives trans-[(2-[(2'-hydroxy[1,1':3',-1''-terphenyl]-5'-yl)thio]cyclohexyl]thio]-N-methyl-N-(2-pyridinylethyl)acetamide;

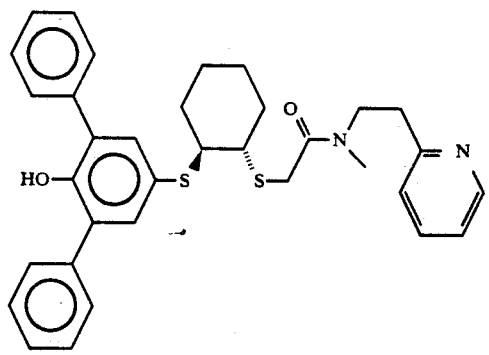

(c) Substituting in Example 21 and following the procedure therein gives trans-[[4-[(2'-hydroxy[1,1':3',1'-terphenyl]-5'-yl)thio]tetrahydro-3-furanyl]oxy]acetic acid;

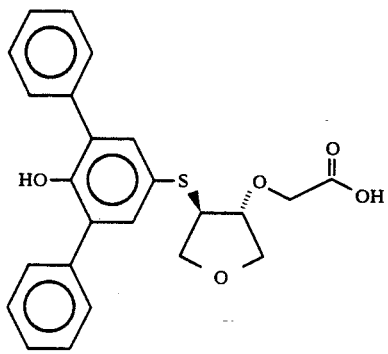

(d) Substituting in Example 20 and following the procedure therein gives trans-[[2-[(2'-hydroxy[1,1':3',1'-terphenyl]-5'-yl)thio]cyclohexyl]oxy]acetic acid.

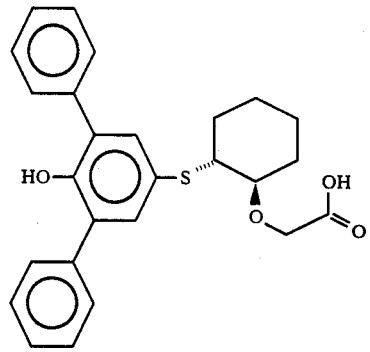

EXAMPLE 37

The following compounds are prepared by replacing 2-(2-methylaminoethyl)pyridine in Example 31 by the following amines listed in (a) through (t) and following the procedure described in Example 31:

(a) Starting with 2-(aminomethyl)pyridine gives: trans-2-[[2-[[3,5-bis(1,1-dimethylethyl)-4-hydroxyphenyl]thio]cyclohexyl]thio]-N-(2-pyridinylmethyl)acetamide;

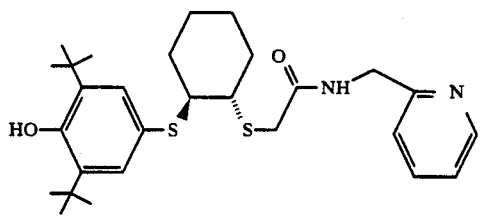

(b) Starting with 3-(aminomethyl)pyridine gives: trans-2-[[2-[[3,5-bis(1,1-dimethylethyl)-4-hydroxyphenyl]thio]cyclohexyl]thio]-N-(3-pyridinylmethyl)acetamide;

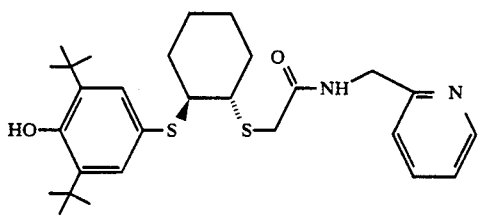

(c) Starting with 3-(methylaminomethyl)pyridine gives: trans-2-[[2-[[3,5-bis(1,1-dimethylethyl)-4-hydroxyphenyl]thio]cyclohexyl]thio]-N-methyl-N-(3-pyridinylmethyl)acetamide;

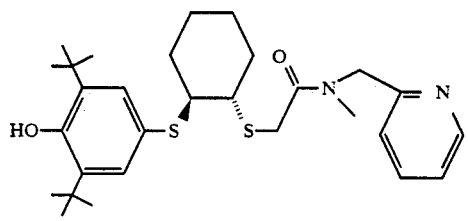

(d) Starting with 4-(aminomethyl)pyridine gives: trans-2-[[2-[[3,5-bis(1,1-dimethylethyl)-4-hydroxyphenyl]thio]cyclohexyl]thio]-N-(4-pyridinylmethyl)acetamide;

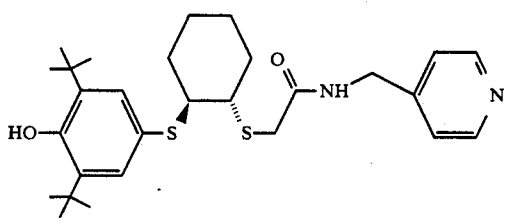

(e) Starting with N-methylpiperazine gives: trans-1-[2-[[2-[[3,5-bis(1,1-dimethylethyl)-4-hydroxyphenyl]thio]cyclohexyl]thio]-1-oxoethyl]-4-methylpiperazine;

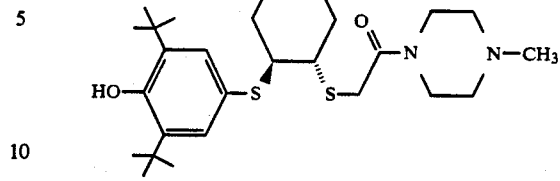

(f) Starting with 1-benzylpiperazine gives: trans-1-[2-[[2-[[3,5-bis(1,1-dimethylethyl)-4-hydroxyphenyl]thio]cyclohexyl]thio]-1-oxoethyl]-4-(phenylmethyl)piperazine;

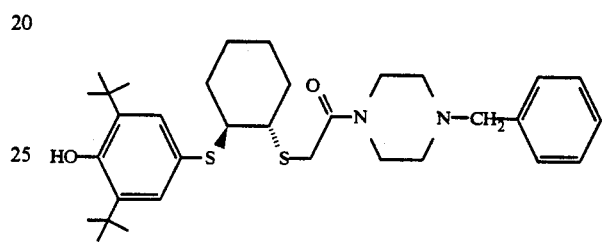

(g) Starting with 4-piperidinopiperidine gives: trans-1-[2-[[2-[[3,5-bis(1,1-dimethylethyl)-4-hydroxyphenyl]thio]cyclohexyl]thio]-1-oxoethyl]-4-(1-piperidinyl)piperidine;

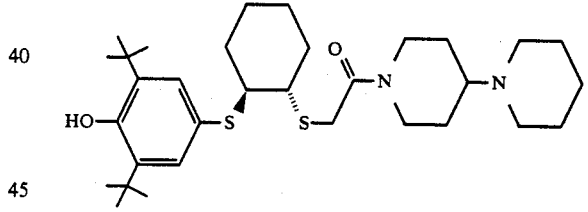

(h) Starting with 4'-piperazinoacetophenone gives: trans-1-(4-acetylphenyl)-4-[2-[[2-[[3,5-bis(1,1-dimethylethyl)-4-hydroxyphenyl]thio]cyclohexyl]thio]-1-oxoethyl]piperazine;

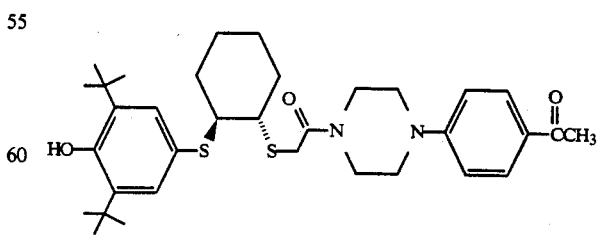

(i) Starting with morpholine gives: trans-4-[2-[[2-[[3,5-bis(1,1-dimethylethyl)-4-hydroxyphenyl]thio]cyclohexyl]thio]-1-oxoethyl]morpholine;

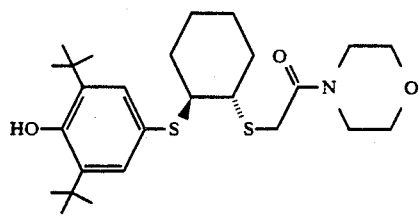

(j) Starting with piperidine gives: trans-1-[2-[[2-[[3,5-bis(1,1-dimethylethyl)-4-hydroxyphenyl]thio]cyclohexyl]thio]-1-oxoethyl]piperidine;

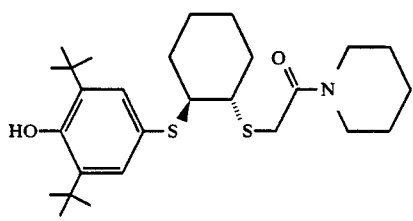

(k) Starting with 3-axabicyclo[3,2,2]nonane gives: trans-3-[2-[[2-[[3,5-bis(1,1-dimethylethyl)-4-hydroxyphenyl]thio]cyclohexyl]thio]-1-oxoethyl]-3-azabicyclo]3.2.2]nonane;

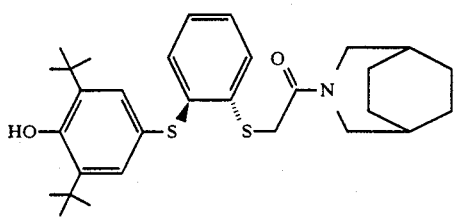

(l) Starting with 3,3-dimethylpiperidine gives: trans-1-[2-[[2-[[3,5-bis (1,1-dimethylethyl)-4-hydroxyphenyl]thio]cyclohexyl]thio]-1-oxoethyl]-3,3dimethylpiperidine;

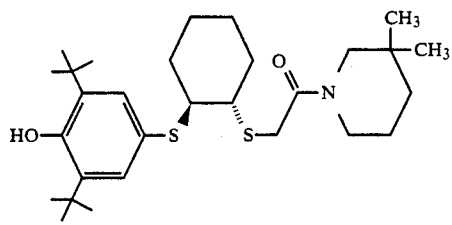

(m) Starting with 1-adamantanamine gives: trans-2-[[2-[[3,5-bis(1,1-dimethylethyl)-4-hydroxyphenyl]thio]cyclohexyl]thio]-N-tricyclo[3.3.1.1$^{3,7}$]dec-1-ylacetamide;

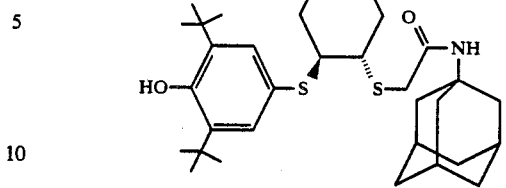

(n) Starting with 1-adamantanemethylamine gives: trans-2-[[2-[[3,5-bis(1,1-dimethylethyl)-4hydroxyphenyl]thio]cyclohexyl]thio]-N-(tricyclo[3.3.1.1$^{3,7}$]dec-1-ylmethyl)acetamide

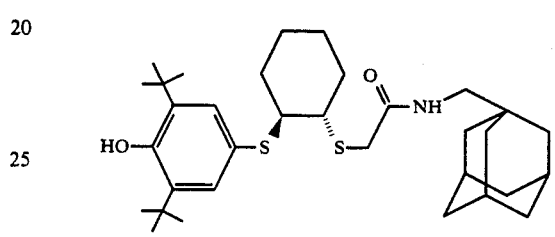

(o) Starting with 4-cyclohexylpiperidine gives: trans-1-[2-[[2-[[3,5-bis(1,1-dimethylethyl)-4-hydroxyphenyl]thio]cyclohexyl]thio]-1-oxoethyl]-4-cyclohexylpiperidine;

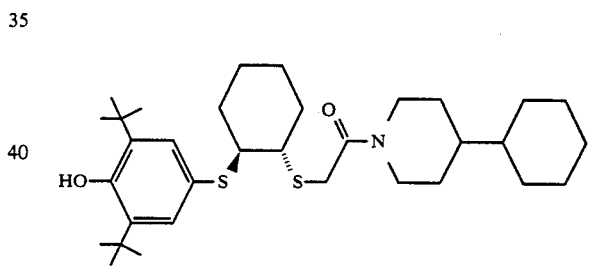

(p) Starting with 2-aminonorbornane (exo or endo) gives: tans-2-[[2-[[3,5-bis(1,1-dimethylethyl)-4-hydroxyphenyl]thio]cyclohexyl]thio]-N-bicyclo[2.2.1]hept-2-ylacetamide;

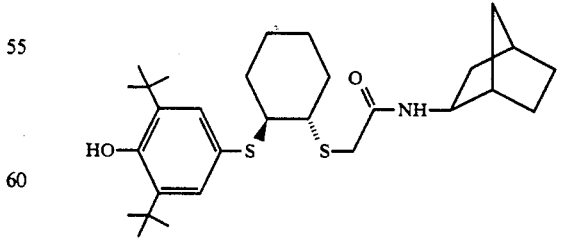

(q) Starting with 1,2,3,4-tetrahydroisoquinoline gives: trans-2-[2-[[2-[[3,5-bis(1,1-diemthylethyl)-4-hydroxyphenyl]thio]cylcohexyl]thio]-1-oxoethyl]-1,2,3,4-tetrahydroisoquinoline;

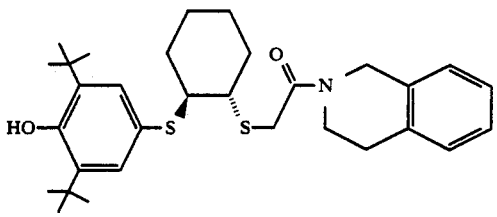

(r) Starting with 5,6,11,12-tetrahydrodibenz[b,f]azocine gives: trans-5[2-[[2-[[3,5-bis (1,1-dimethylethyl)-4-hydroxyphenyl]thio]cyclohexyl]thio]-1-oxoethyl]-5,6,11,12-tetrahydrodibenz[b,f]azocine;

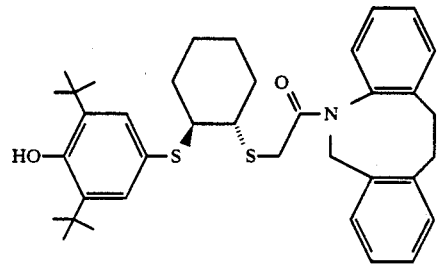

(s) Starting with iminostilbene gives: trans-5-[2-[[2-[[3,5-bis(1,1-dimethylethyl)-4-hydroxyphenyl]thio]cyclohexyl]thio -1-oxoethyl]-5H-dibenz[b,f]azepine;

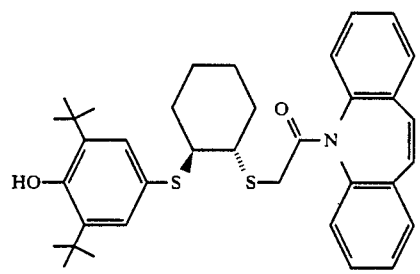

(t) Starting with N-methyl-N-butylamine gives: trans-2-[[2-[[3,5-bis(1,1-dimethylethyl)-4-hydroxyphenyl]thio]cyclohexyl]thio]-N-butyl-N-methylacetamide.

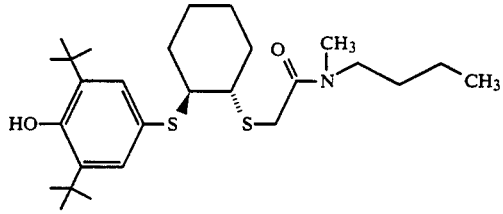

EXAMPLE 38

Substituting the starting compounds named in (a), (b) and (c) below for the trans-[[2-[[3,5-bis(1,1-dimethylethyl)-4-hydroxyphenyl]thio]cyclohexyl]thio]acetic acid in Example 37 and following the procedures described therein gives the corresponding amides:

(a) trans-[[2-[[3,5-bis(1,1-dimethylethyl)-4-hydroxyphenyl]thio]cyclopentyl]thio]acetic acid;

(b) trans-[[2-[[3,5-bis(1,1-dimethylethyl)-4-hydroxyphenyl]thio]cyclohexyl]oxy]acetic acid;

(c) trans-[[2-[[3,5-bis(1,1-dimethylethyl)-4-hydroxyphenyl]thio]tetrahydro-3-furanyl]oxy]acetic acid.

EXAMPLE 39

Utilizing the foregoing synthesis methods and appropriate starting materials, the following compounds are likewise obtained:

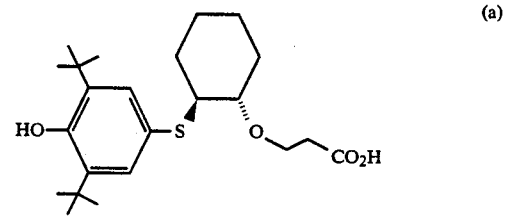

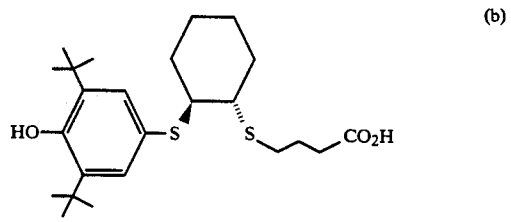

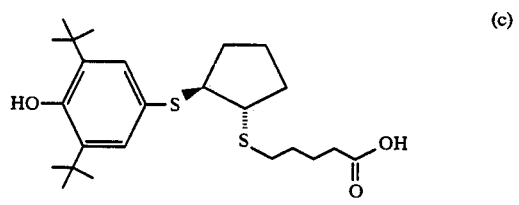

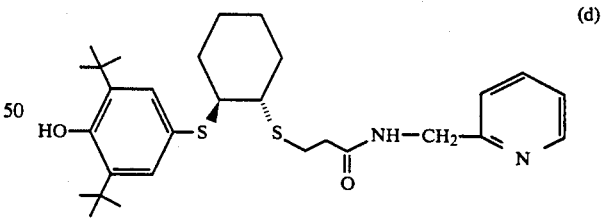

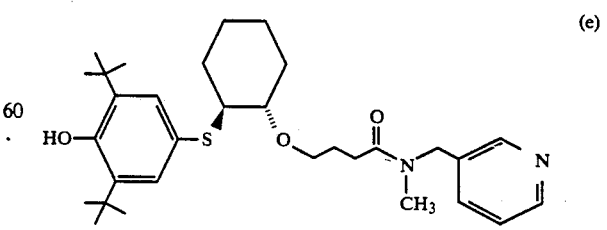

What is claimed is:

1. A compound of the formula:

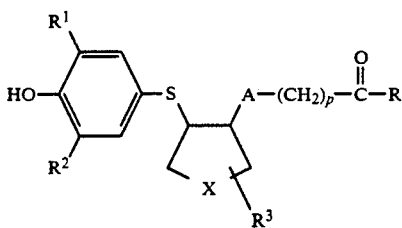

where $R^1$ and $R^2$ are the same or different and independently represent tert-alkyl or phenyl; $R^3$ represents hydrogen or alkyl; x represents —$(CH_2)_w$-B-$(CH_2)_y$— wherein B represents O and w and y can each independently be an integer from 0 to 3 with the proviso that the sum of w+y is equal to or less than 3; A represents O or $S(O)_n$ wherein n is 0, 1, or 2; p is an integer from 0 to 4; and R represents:
(a) alkyl;
(b) OH;
(c) $OR^4$ wherein $R^4$ is alkyl of 1 to 4 carbon atoms;
(d) $(CH_2)_tCOOR^7$ wherein t is an integer from 1 to 4 and $R^7$ is hydrogen or alkyl of 1 to 4 carbon atoms;
or a pharmaceutically acceptable salt thereof.

2. A compound according to claim 1 of the formula

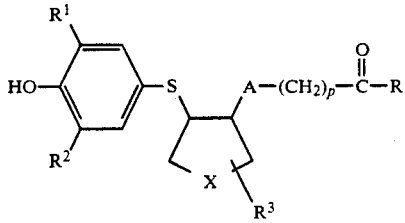

wherein $R^1$ and $R^2$ are the same or different and independently represent tert-alkyl or phenyl; $R^3$ represents hydrogen or alkyl of 1 to 4 carbon atoms; X represents O; A represents O or $S(O)_n$ wherein n is 0, 1, or 2; p is an integer from 0 to 4; and R represents:
(a) alkyl of 1 to 4 carbon atoms;
(b) OH;
(c) $OR^4$ wherein $R^4$ is alkyl of 1 to 4 carbon atoms;
(d) $(CH_2)_tCOOR^7$ wherein t is an integer from 1 to 4 and $R^7$ is hydrogen or alkyl of 1 to 4 carbon atoms;
or a pharmaceutically acceptable salt thereof.

3. A compound according to claim 2 of the formula

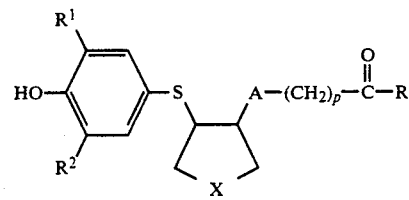

wherein $R^1$ and $R^2$ are the same or different and independently represent tert-alkyl or phenyl; X is 0; A is S or O; p is an integer from 0 to 2, and R is:
(a) alkyl of 1 to 4 carbon atoms;
(b) OH;
(c) $OR^4$ wherein $R^4$ is alkyl of 1 to 4 carbon atoms; or a pharmaceutically acceptable salt thereof.

4. A compound according to claim 3 wherein $R^1$ and $R^2$ are tert-alkyl; A is sulfur; p is 1 or 2; and R is:

(a) OH;
(b) $OR^4$ wherein $R^4$ is alkyl of 1 to 4 carbon atoms; or a pharmaceutically acceptable slat thereof.

5. A compound according to claim 1 wherein $R^1$ and $R^2$ are tert-butyl.

6. A compound according to claim 3 wherein $R^1$ and $R^2$ are tert-butyl.

7. A compound according to claim 2 which is trans-[[4-[[3,5-bis(1,1-dimethylethyl)-4-hydroxyphenyl]thio]-tetrahydro-3-furanyl]oxy]acetic acid.

8. A compound according to claim 1 which is trans-4-[[3,5-bis(1,1-dimethylethyl)-4-hydroxyphenyl]thio]tetrahydro-3-furanol, acetate.

9. A compound according to claim 1 which is butanedioic acid, trans-mono[4-[[3,5-bis(1,1-dimethylethyl)4-hydroxyphenyl]thio]tetrahydro-3-furanyl]ester.

10. A pharmaceutical composition for use in the treatment of lipoxygenase mediated conditions which comprises a therapeutically effective amount of compound of the formula

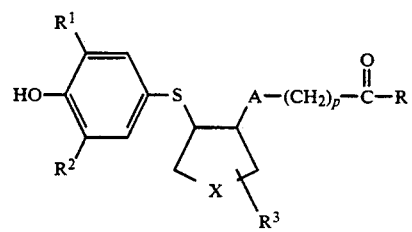

wherein $R^1$ and $R^2$ are the same or different and independently represent tert-alkyl or phenyl; $R^3$ represents hydrogen or alkyl; X represents —$(CH_2)_w$—B—$(CH_2)_y$— wherein B represents O and w and y can each independently be an integer from 0 to 3 with the proviso that the sum of w+y is equal to or less than 3; A represents O or $S(O)_n$ wherein n is 0, 1, or 2; p is an integer form 0 to 4; and R represents;
(a) alkyl;
(b) OH;
(c) $OR^4$ wherein $R^4$ is alkyl of 1 to 4 carbon atoms;
(d) $(CH_2)_tCOOR^7$ wherein t is an integer from 1 to 4 and $R^7$ is hydrogen or alkyl of 1 to 4 carbon atoms;
or a pharmaceutically acceptable salt thereof; and a pharmaceutically acceptable carrier.

11. A pharmaceutical composition according to claim 10 for use in the treatment of inflammation and allergy comprising a therapeutically effective amount of a compound of the formula

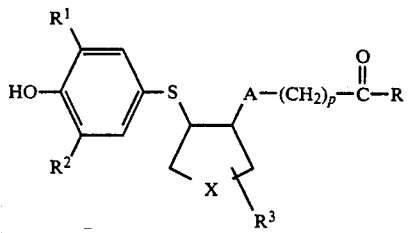

wherein $R^1$ and $R^2$ are the same or different and independently represent tert-alkyl or phenyl; $R^3$ represents hydrogen or alkyl; X represents —$(CH_2)_w$—B—$(CH_2)_y$— wherein B represents O or S and w and y can each independently be an integer from 0 to 3 with the proviso that the sum of w+y is equal to or less than 3; A represents O or S(O)$_n$ wherein n is 0, 1, or 2; p is an integer from 0 to 4; and R represents:
(a) alkyl;
(b) OH;
(c) OR$^4$ wherein R$^4$ is alkyl of 1 to 4 carbon atoms;
(d) (CH$_2$)$_t$COOR$^7$ wherein t is an integer from 1 to 4 and R$^7$ is hydrogen or alkyl of 1 to 4 carbon atoms;

or a pharmaceutically acceptable salt thereof; and a pharmaceutically acceptable carrier.

12. A method of treating lipoxygenase mediated conditions which comprises administering to a patient in need of such treatment a therapeutically effective amount of a compound of the formula

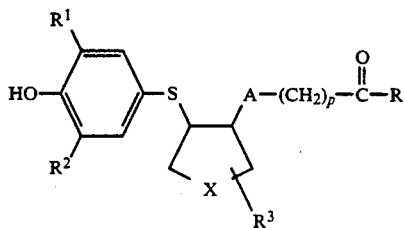

wherein R$^1$ and R$^2$ are the same or different and independently represent tert-alkyl or phenyl; R$^3$ represents hydrogen or alkyl; X represents —(CH$_2$)$_w$—B—(CH$_2$)$_y$— wherein B represents O and w and y can each independently be an integer from 0 to 3 with the proviso that the sum of w+y is equal to or less than 3; A represents O or S(O)$_n$ wherein n is 0, 1, or 2; p is an integer from 0 to 4; and R represents:
(a) alkyl;
(b) OH;
(c) OR$^4$ wherein R$^4$ is alkyl of 1 to 4 carbon atoms;
(d) (CH$_2$)$_t$COOR$^7$ wherein t is an integer from 1 to 4 and R$^7$ is hydrogen or alkyl of 1 to 4 carbon atoms;

or a pharmaceutically acceptable salt thereof.

13. A method of treating inflammation which comprises administering to a patient in need of such treatment a therapeutically effective amount of a compound of the formula

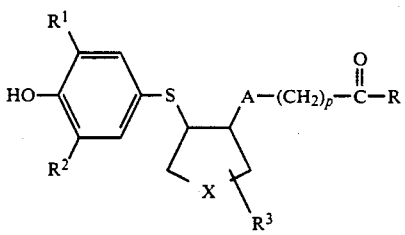

wherein R$^1$ and R$^2$ are the same or different and independently represent tert-alkyl or phenyl; R$^3$ represents hydrogen or alkyl; X represents —(CH$_2$)$_w$—B—(CH$_2$)$_y$— wherein B represents O and w and y can each independently be an integer from 0 to 3 with the proviso that the sum of w+y is equal to or less than 3; A represents O or S(O)$_n$ wherein n is 0, 1, or 2; p is an integer form 0 to 4; and R represents:
(a) alkyl;
(b) OH;
(c) OR$^4$ wherein R$^4$ is alkyl of 1 to 4 carbon atoms;
(d) (CH$_2$)$_t$COOR$^7$ wherein t is an integer from 1 to 4 and R$^7$ is hydrogen or alkyl of 1 to 4 carbon atoms;

or a pharmaceutically acceptable salt thereof.

14. A method of treating allergic reactions which comprises administering to a patient in need of such treatment a therapeutically effective amount of a compound of the formula

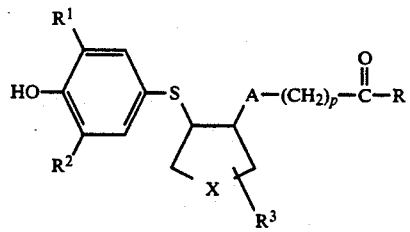

wherein R$^1$ and R$^2$ are the same or different and independently represent tert-alkyl or phenyl; R$^3$ represents hydrogen or alkyl; X represents —(CH$_2$)$_w$—B—(CH$_2$)$_y$— wherein B represents O and w and y can each independently be an integer from 0 to 3 with the proviso that the sum of w+y is equal to or less than 3; A represents O or SO$_n$ wherein n is 0, 1, or 2; p is an integer from 0 to 4; and R represents:
(a) alkyl;
(b) OH;
(c) OR$^4$ wherein R$^4$ is alkyl of 1 to 4 carbon atoms;
(d) (CH$_2$)$_t$COOR$^7$ wherein t is an integer from 1 to 4 and R$^7$ is hydrogen or alkyl of 1 to 4 carbon atoms;

or a pharmaceutically acceptable salt thereof.

15. A method according to claim 13 wherein said inflammation is arthritis.

16. A method according to claim 13 wherein said inflammation is psoriasis.

17. A pharmaceutical composition according to claim 11 wherein said compound is selected from the group consisting of
trans-[[4-[[3,5-bis(1,1-dimethylethyl)-4-hydroxyphenyl]thio]tetrahydro-3-furanyl]oxy]acetic acid;
trans-4-[[3,5-bis(1,1-dimethylethyl)-4-hydroxyphenyl]thio]tetrahydro-3-furanol, acetate; and
butanedioic acid, trans-mono[4-[[3,5-bis(1,1-dimethylethyl)-4-hydroxyphenyl]thio tetrahydro-3-furanyl]-ester.

18. A method according to claim 13 wherein said compound is selected from the group consisting of
trans-[[4-[[3,5-bis (1,1-dimethylethyl)-4-hydroxyphenyl]thio]tetrahydro-3-furanyl]oxy]acetic acid;
trans-4-[[3,5-bis(1,1-dimethylethyl)-4-hdyroxyphenyl]thio]tetrahydro-3-furanol, acetate; and
butanedioic acid, trans-mono[4-[[3,5-bis(1,1-dimethylethyl)-4-hydroxyphenyl]thio]tetrahydro-3-furanyl]-ester.

19. A method according to claim 14 wherein said compound is selected from the group consisting of
trans-[[4-[[3,5-bis(1,1-dimethylethyl)-4-hydroxyphenyl]thio]tetrahydro-3-furanyl]oxy]acetic acid;
trans-4-[[3,5-bis(1,1-diemthylethyl)-4-hdyroxyphenyl]thio]tetrahydro-3-furanol, acetate; and
butanedioic acid, trans-mono[4-[[3,5-bis(1,1-dimethylethyl)-4-hydroxyphenyl]thio]tetrahydro-3-furnayl]-ester.

* * * * *

UNITED STATES PATENT AND TRADEMARK OFFICE
CERTIFICATE OF CORRECTION

PATENT NO. : 5,250,567  
DATED : October 5, 1993  
INVENTOR(S) : Mueller, et al.

Page 1 of 3

It is certified that error appears in the above-indentified patent and that said Letters Patent is hereby corrected as shown below:

Column 2, line 42, reading "of-these" should read --of these--.

Column 5, line 12, reading "568-574.°" should read --568-574.--.

Column 5, line 37, reading "object-of" should read --object of--.

Column 6, line 28, reading "$H_2O_2$,.OH," should read --$H_2O_2$, OH,--.

Column 6, line 64, reading "slats" should read --salts--.

Column 11, line 2, reading "product" should read --product.--.

Column 15, line 28, reading "[i-$^{14}$C)" should read --[1-$^{14}$C)--.

Column 15, line 63, reading "Neutroohils" should read --Neutrophils--.

Column 16, line 68, reading "an stimulated" should read --and stimulated--.

Column 24, line 40, reading "supported-by" should read --supported by--.

Column 25, line 7, reading "8.4I;" should read --8.41;--.

Column 26, line 36, reading "for ethyl" should read --from ethyl--.

Column 26, line 44, reading "(1,1Dimethylethyl)" should read --(1,1-Dimethylethyl)--.

UNITED STATES PATENT AND TRADEMARK OFFICE
CERTIFICATE OF CORRECTION

PATENT NO. : 5,250,567
DATED : October 5, 1993
INVENTOR(S) : Mueller, et al.

It is certified that error appears in the above-indentified patent and that said Letters Patent is hereby corrected as shown below:

Column 27, line 56, reading "mole).was" should read --mole)was--.

Column 30, line 10, that part of the formula reading

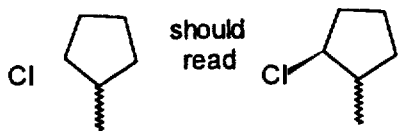

Column 32, line 49, reading "1Δ" should read --1"--.

Column 33, line 65, reading "trans-[(2-" should read --trans-[[2---.

Column 34, line 19, reading "1,1':3','-" should read --1,1':3',1"- --.

Column 34, line 40, reading "1,1':3','-" should read --1,1':3',1"- --.

Column 37, line 29, reading "3-axabicyclo" should read --3-azabicyclo--.

Column 37, line 49, reading "3,3dimethylpiperidine;" should read --3,3-dimethylpiperidine;--.

Column 38, line 15, reading "4hydroxy-" should read --4-hydroxy---.

Column 38, line 48, reading "tans-2-" should read --trans-2---.

Column 41, line 12, reading "where" should read --wherein--.

Column 41, line 14, reading "x" should read --X--.

UNITED STATES PATENT AND TRADEMARK OFFICE
CERTIFICATE OF CORRECTION

PATENT NO. : 5,250,567
DATED : October 5, 1993
INVENTOR(S) : Mueller, et al.

It is certified that error appears in the above-indentified patent and that said Letters Patent is hereby corrected as shown below:

Column 42, line 3, reading "slat" should read --salt--.
Column 43, line 6, reading "(CH$_2$)COOR$^7$" should read --(CH$_2$)$_t$COOR$^7$--
Column 43, line 62, reading "form" should read --from--.
Column 44, line 25, reading "S( )$_n$" should read --S(O)$_n$--.
Column 44, line 45, reading "thio" should read --thio]--.
Column 44, line 51, reading "hdyroxyphenyl" should read --hydroxyphenyl--.

Signed and Sealed this

Seventeenth Day of June, 1997

BRUCE LEHMAN

Attest:

Attesting Officer

Commissioner of Patents and Trademarks